US006475752B1

(12) United States Patent
Lal et al.

(10) Patent No.: US 6,475,752 B1
(45) Date of Patent: Nov. 5, 2002

(54) MAMMALIAN IMIDAZOLINE RECEPTOR

(75) Inventors: Preeti Lal, Santa Clara, CA (US); Y. Tom Tang, San Jose, CA (US); Mariah R. Baughn, San Leandro, CA (US); Matthew R. Kaser, Castro Valley, CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/364,206

(22) Filed: Jul. 30, 1999

(51) Int. Cl.[7] .......................... C12P 21/06; C12P 21/04; C12N 1/20; C12N 15/00; C07H 21/04
(52) U.S. Cl. .................... 435/69.1; 435/70.1; 435/71.1; 435/71.2; 435/252.3; 435/320.1; 435/325; 435/471; 435/6; 536/23.5
(58) Field of Search ................................ 435/69.1, 70.1, 435/71.1, 71.2, 252.3, 320.1, 325, 471, 6; 536/23.5

(56) References Cited

U.S. PATENT DOCUMENTS 5,350,836 A * 9/1994 Kopchick et al.
6,015,690 A * 1/2000 Piletz et al.

OTHER PUBLICATIONS

Vukicevic et al. PNAS USA 93:9021–9026, 1996.*
Massague J. Cell 49:437–8, 1987.*
Pilbeam et al. Bone 14:717–720, 1993.*
Skolnick et al. Trends in Biotech. 18:34–39, 2000.*
Bork P. Genome Research 10:398–400, 2000.*
Doerks et al. Trends in Genetics 14:248–250, 1998.*
Smith et al. Nature Biotechnology 15:1222–1223, 1997.*
Brenner SE. Trends in Genetics 15: 132–133, 1999.*
Bork et al. Trends in Genetics 12:425–427, 1996.*
Hudson T. Database GenEmbl. Accession No. G24322, May. 31, 1996.*
Herman, Z.S., "Agmatine—A Novel Endogenous Ligand of Imidazoline Receptors", *Pol. J. Pharmacol.*, 49:85–88 (1997).
Ivanov, T.R. et al., GeneSeq output W43396 (May 01, 1998).
Bolton, A.E. and W.M. Hunter, "The Labeling of Proteins to High Specific Radioactivities by Conjugation to a $^{125}$I–Containing Acylating Agent", *Biochem. J.*, 133:529–539 (1973).
Agostino, M.J. et al., GeneSeq output W29677 (Nov. 9, 1998).
Piletz, J.E. et al., (Direct Submission), GenBank Sequence Database (Accession AF058290), National Center for Biotechnology Information, National Library of Medicine, Bethesda, Maryland, 20894 (GI 3493224) (Aug. 30, 1998).
Piletz, J.E. et al., (Direct Submission), GenBank Sequence Database (Accession 3462807), National Center for Biotechnology Information, National Library of Medicine, Bethesda, Maryland, 20894 (GI 3462807) (Aug. 18, 1998).

* cited by examiner

Primary Examiner—Gary L. Kunz
Assistant Examiner—Robert S. Landsman
(74) Attorney, Agent, or Firm—Incyte Genomics, Inc.

(57) ABSTRACT

The invention provide a mammalian nucleic acid molecule and fragments thereof. It also provides for the use of the mammalian nucleic acid molecule for the characterization, diagnosis, evaluation, treatment, or prevention of conditions, diseases and disorders associated with its expression and for the production of a model system. The invention additionally provides expression vectors and host cells for the production of the protein encoded by the mammalian nucleic acid molecule. The invention further provides a mammalian protein or portions thereof. The invention still further provides for the use of the nucleic acid molecule and protein in assays to detect or purify ligands.

12 Claims, 21 Drawing Sheets

```
5' GGT GGC GGA GAC CCG AAC ATG GCG ACC GCG ACC TTC GGG CCC GAG CGG         54

GAA GCC GAG CCG GCC AAG GAA GCG CGC ACC TTC GGG CCC GAG CGG           108
     E   A   E   P   A   K   E   A   R   T   F   G   P   E   R

TAT ACG GTT TAC ATC CAG GTC GTG GGC TCG GAG CTT GTG GAC ACT           162
     Y   T   V   Y   I   Q   V   V   G   S   E   L   V   D   T

CAC CGC TAC AGC GAC TTC CAT GAC ACT GAT GGC AGC CAT GAG TGG ACA GTA AAG   216
     H   R   Y   S   D   F   H   D   T   D   G   S   H   E   W   T   V   K

ATT GAT AAA AAC CTG CTT CCG CCC AAA AAG ATA ATT GGG AAA CTC GTT GCA GAG AGA AAG  270
     I   D   K   N   L   L   P   P   K   K   I   I   G   K   L   V   A   E   R   K

TTG GTG GAG AAG AGG GAG AAG GAT CTG GAG GTC TAC CTC CAG AAG CTC CTG GCT   324
     L   V   E   K   R   E   K   D   L   E   V   Y   L   Q   K   L   L   A

GCC TTC CCT GGC GTG ACC CCC AGA GTA CTG GCC CAC TTC TTG CAT TTT CAC TTC   378
     A   F   P   G   V   T   P   R   V   L   A   H   F   L   H   F   H   F
```

FIGURE 1A

```
                387              396         405         414         423         432
TAT GAG ATA AAT GGC ATC ACC GCG GCA CTG GCT GAA GAG CTC TTT GAG AAA GGA
 Y   E   I   N   G   I   T   A   A   L   A   E   E   L   F   E   K   G 441         450         459         468         477         486
GAA CAG CTC CTG GGG GCC GGC GAG TTT GCC ATT GGA CCC CTG CAG CTG TAT
 E   Q   L   L   G   A   G   E   F   A   I   G   P   L   Q   L   Y 495         504         513         522         531         540
GCC GTC ACG GAG CAG CAG CTG CAG CAG GGA AAG CCC ACG TGC GCC AGT GGG GAT GCC
 A   V   T   E   Q   Q   L   Q   Q   G   K   P   T   C   A   S   G   D   A 549         558         567         576         585         594
AAG ACC GAC CTC GGG CAC ATC CTG GAC TTC ACC TGT CGC CTT AAG TAC CTT AAG
 K   T   D   L   G   H   I   L   D   F   T   C   R   L   K   Y   L   K 603         612         621         630         639         648
GTT TCT GGC ACA GAA GGA CCT TTT GGG ACC AGC AAC ATT CAG GAG CAG CTC CTG
 V   S   G   T   E   G   P   F   G   T   S   N   I   Q   E   Q   L   L 657         666         675         684         693         702
CCG TTC GAC CTA TCA ATA TTC AAG TCC CTG CAT CAG GTG GAG ATA AGT CAC TGT
 P   F   D   L   S   I   F   K   S   L   H   Q   V   E   I   S   H   C 711         720         729         738         747         756
GAT GCT AAG CAC ATC AGA GGG CTG GTC GCA TCG AAG CCC ACC TTA GCC ACG CTG
 D   A   K   H   I   R   G   L   V   A   S   K   P   T   L   A   T   L
```

FIGURE 1B

```
        765            774           783           792           801           810
AGT GTC CGC TTC TCA GCA ACC TCG ATG AAG GAA GTC CTT GTT CCT GAA GCC TCA
 S   V   R   F   S   A   T   S   M   K   E   V   L   V   P   E   A   S 819            828           837           846           855           864
GAA TTT GAT GAG TGG GAG CCT GAA ACA GGC CTA GAA GGC CCT GTG ACT GCC
 E   F   D   E   W   E   P   E   T   G   L   E   G   P   V   T   A 873            882           891           900           909           918
GTC ATC CCC ACT TGG CAG GCA TTG ACC ACG CTT GAC CTG AGC AAC AGC ATC
 V   I   P   T   W   Q   A   L   T   T   L   D   L   S   N   S   I 927            936           945           954           963           972
TCC GAG GAC GAG TCT GTG AAA CTG ATC CCA AAG ATT GAG TTC CTG GAC CTG
 S   E   D   E   S   V   K   L   I   P   K   I   E   F   L   D   L 981            990           999          1008          1017          1026
AGT CAC AAT GGA TTG CTG GTT GTG GAC AAT CTG CAG CAC CTG TAT AAC CTT GTG
 S   H   N   G   L   L   V   V   D   N   L   Q   H   L   Y   N   L   V 1035           1044          1053          1062          1071          1080
CAT CTG GAC CTG TCC TAC AAC AAG CTC TCC TCC TTG GAA GGG CTT CAC ACC AAG
 H   L   D   L   S   Y   N   K   L   S   S   L   E   G   L   H   T   K 1089           1098          1107          1116          1125          1134
CTG GGG AAC ATC AAG ACC TTA AAC CTG GCA GGC AAC CTC CTA GAG AGT CTG AGT
 L   G   N   I   K   T   L   N   L   A   G   N   L   L   E   S   L   S

FIGURE 1C
```

```
    1143          1152          1161          1170          1179          1188
GGC CTG CAC AAG CTC TAC TCA CTG GTC AAC CTG GAT CTC CGG GAC AAC AGG ATC
 G   L   H   K   L   Y   S   L   V   N   L   D   L   R   D   N   R   I 1197          1206          1215          1224          1233          1242
GAA CAG ATG GAG GAG GTC CGG AGC ATA GGC CTC CCG TGT CTG GAG CAC GTG
 E   Q   M   E   E   V   R   S   I   G   L   P   C   L   E   H   V 1251          1260          1269          1278          1287          1296
TCT CTG AAC AAC CCT CTG AGC ATC ATC CCC GAC TAC CGG ACC AAG GTG CTG
 S   L   N   N   P   L   S   I   I   P   D   Y   R   T   K   V   L 1305          1314          1323          1332          1341          1350
GCT CAG TTC GGA GAG AGG GCC TCA GAG GTC TGT CTG GAT GAC ACA GTG ACC ACA
 A   Q   F   G   E   R   A   S   E   V   C   L   D   D   T   V   T   T 1359          1368          1377          1386          1395          1404
GAG AAG GAG CTG GAC ACT GTG GAA GTG CTG AAA GCA ATT CAG AAA GCC AAG GAG
 E   K   E   L   D   T   V   E   V   L   K   A   I   Q   K   A   K   E 1413          1422          1431          1440          1449          1458
GTC AAG TCC AAA CTG AGC AGC AAC CCA GAG AAG AAG GGT GAA GAC TCC CGG CTC
 V   K   S   K   L   S   S   N   P   E   K   K   G   E   D   S   R   L 1467          1476          1485          1494          1503          1512
TCA GCT GCC CCC TGC ATC AGA CCC ATC AGC AGC TCC CCT CCC ACT GTG GCT CCC GCA
 S   A   A   P   C   I   R   P   I   S   S   S   P   P   T   V   A   P   A
```

FIGURE 1D

```
1521            1530            1539            1548            1557            1566
TCT GCC TCC CTG CCC CAG CCC ATC CTC TCT AAC CAA GGA ATC ATG TTC GTT CAG
 S   A   S   L   P   Q   P   I   L   S   N   Q   G   I   M   F   V   Q 1575            1584            1593            1602            1611            1620
GAG GAG GCC CTG GCC AGC AGC CTC TCG TCC ACT GAC AGT CTG ACT CCC GAG CAC
 E   E   A   L   A   S   S   L   S   S   T   D   S   L   T   P   E   H 1629            1638            1647            1656            1665            1674
CAG CCC ATT GCC CAG GGA TGT TCT GAT TCC TTG GAG TCC ATC CCT GCG GGA CAG
 Q   P   I   A   Q   G   C   S   D   S   L   E   S   I   P   A   G   Q 1683            1692            1701            1710            1719            1728
GCA GCT TCC GAT GAT TTA AGG GAC GTG CCA GGA GCT GTT GGT GCA AGC CCA
 A   A   S   D   D   L   R   D   V   P   G   A   V   G   A   S   P 1737            1746            1755            1764            1773            1782
GAA CAT GCC GAG CCG GAG GTC CAG GTG GTG CCG GGG TCT GGC CAG ATC ATC TTC
 E   H   A   E   P   E   V   Q   V   V   P   G   S   G   Q   I   I   F 1791            1800            1809            1818            1827            1836
CTG CCC TTC ACC TGC ATT GGC TAC ACG GCC ACC GCC AAT CAG GAC TTC ATC CAG CGC
 L   P   F   T   C   I   G   Y   T   A   T   A   N   Q   D   F   I   Q   R 1845            1854            1863            1872            1881            1890
CTG ACA AGC CTG ATC CGG CAG GCC ATC GAG CGG CAG CTG CCT GCC TGG ATC GAG
 L   T   S   L   I   R   Q   A   I   E   R   Q   L   P   A   W   I   E
```

FIGURE 1E

```
      1899            1908            1917            1926            1935            1944
GCT GCC AAC CAG CGG GAG GAG GGC CAG GGT GAA CAG GGC GAG GAG GAG GAT GAG
 A   A   N   Q   R   E   E   G   Q   G   E   Q   G   E   E   E   D   E 1953            1962            1971            1980            1989            1998
GAG GAG GAA GAG GAG GAC GTG GCT GAG AAC CGC TAC TTT GAA ATG GGG CCC
 E   E   E   E   E   D   V   A   E   N   R   Y   F   E   M   G   P 2007            2016            2025            2034            2043            2052
CCA GAC GTG GAG GAG GGA GGC CAG GGA GAG AAC CGC TAC TTT GAA ATG GGG CCC
 P   D   V   E   E   G   G   Q   G   E   E   E   E

CCA GAC GTG GAG GAG GAG GGA GGC CAG GGA GAG GAG GAG GAG GAG GAA
 P   D   V   E   E   E   G   G   Q   G   E   E   E   E   E   E 2061            2070            2079            2088            2097            2106
GAG GAG GAT GAA GAG GCC GAG CGC CTG GCT CTG GAA TGG GCC CTG GGC
 E   E   D   E   E   A   E   R   L   A   L   E   W   A   L   G 2115            2124            2133            2142            2151            2160
GCG GAC GAG GAC TTC CTG CTG GAG CAC ATC CGC ATC CTC AAG GTG CTG TGC
 A   D   E   D   F   L   L   E   H   I   R   I   L   K   V   L   C 2169            2178            2187            2196            2205            2214
TTC CTG ATC CAT GTG CAG GGC AGT ATC CGC TTC GCC GCC TGC CTT GTG CTC
 F   L   I   H   V   Q   G   S   I   R   Q   F   A   A   C   L   V   L 2223            2232            2241            2250            2259            2268
ACC GAC TTC GGC ATC GCA GTC TTC GAG ATC CCG CAC CAG GAG TCT CGG GGC AGC
 T   D   F   G   I   A   V   F   E   I   P   H   Q   E   S   R   G   S
```

FIGURE 1F

```
     2277              2286              2295              2304              2313              2322
AGC  CAG  CAC  ATC  CTC  TCC  CTG  CGC  TTT  GTC  TTT  TGC  TTC  CCG  CAT  GGC  GAC
 S    Q    H    I    L    S    L    R    F    V    F    C    F    P    H    G    D 2331              2340              2349              2358              2367              2376
CTC  ACC  GAG  TTT  GGC  TTC  CTC  ATG  CCG  GAG  CTG  TGT  CTG  GTG  CTC  AAG  GTA  CGG
 L    T    E    F    G    F    L    M    P    E    L    C    L    V    L    K    V    R 2385              2394              2403              2412              2421              2430
CAC  AGT  GAG  AAC  ACG  CTC  TTC  ATT  ATC  TCG  GAC  GCC  GCC  AAC  CTG  CAC  GAG  TTC
 H    S    E    N    T    L    F    I    I    S    D    A    A    N    L    H    E    F 2439              2448              2457              2466              2475              2484
CAC  GCG  GAC  CTG  CGC  TCA  TGC  TTT  GCA  CCC  CAG  CAG  ATG  GCC  ATG  CTG  TGT  AGC
 H    A    D    L    R    S    C    F    A    P    Q    Q    M    A    M    L    C    S 2493         2502         2511         2520         2529         2538
CCC  ATC  CTC  TAC  GGC  AGC  AGC  CAC  ACC  AGC  CTG  CAG  GAG  TTC  CTG  CGC  CAG  CTG  CTC
 P    I    L    Y    G    S    S    H    T    S    L    Q    E    F    L    R    Q    L    L 2547              2556              2565              2574              2583              2592
ACC  TTC  TAC  AAG  GTG  GCT  GGC  GGC  TGC  CAG  GAG  CGC  AGC  CAG  CGC  TGC  TTC  CCC
 T    F    Y    K    V    A    G    G    C    Q    E    R    S    Q    R    C    F    P 2601              2610              2619              2628              2637              2646
GTC  TAC  CTG  GTC  TAC  AGT  GAC  AAG  CGC  ATG  GTG  CAG  ACG  GCC  GCC  GGG  GAC  TAC
 V    Y    L    V    Y    S    D    K    R    M    V    Q    T    A    A    G    D    Y
```

FIGURE 1G

```
      2655            2664      2673            2682      2691            2700
TCA GGC AAC ATC GAG TGG GCC AGC TGC ACA CTC TGT TCA GCC GTG CGG CGC TCC
 S   G   N   I   E   W   A   S   C   T   L   C   S   A   V   R   R   S 2709            2718      2727            2736      2745            2754
TGC TGC GCG CCC TCT GAG GCC GTC AAG TCC GCC GCC ATC CCC TAC TGG CTG TTG
 C   C   A   P   S   E   A   V   K   S   A   A   I   P   Y   W   L   L 2763            2772      2781            2790      2799            2808
CTC ACG CCC CAG CAC CTC AAC GTC ATC AAG GCC GAC TTC AAC CCC ATG CCC AAC
 L   T   P   Q   H   L   N   V   I   K   A   D   F   N   P   M   P   N 2817            2826      2835            2844      2853            2862
CGT GGC ACC CAC AAC TGT CGC AAC AGC TTC AAG CTC AGC CGT GTG CCG
 R   G   T   H   N   C   R   N   S   F   K   L   S   R   V   P 2871            2880      2889            2898      2907            2916
CTC TCC ACC GTG CTG CTG GAC CCC ACA CGC AGC TGT ACC CAG CCT CGG GGC GCC
 L   S   T   V   L   L   D   P   T   R   S   C   T   Q   P   R   G   A 2925            2934      2943            2952      2961            2970
TTT GCT GAT GGC CAC GTG CTA GAG CTG CTC GTG GGG TAC CGC TTT GTC ACT GCC
 F   A   D   G   H   V   L   E   L   L   V   G   Y   R   F   V   T   A 2979            2988      2997            3006      3015            3024
ATC TTC GTG CTG CCC CAC GAG AAG TTC CAC TTC CTG CGC GTC TAC AAC CAG CTG
 I   F   V   L   P   H   E   K   F   H   F   L   R   V   Y   N   Q   L
```

FIGURE 1H

FIGURE 11

```
      3033            3042            3051            3060            3069            3078
CGG GCC TCG     CTG CAG GAC     CTG AAG ACT     GTG ATC GCC     AAG ACC CCC     GGG ACG
 R   A   S       L   Q   D       L   K   T       V   I   A       K   T   P       G   T 3087            3096            3105            3114            3123            3132
GGA GGC AGC     CCC CAG GGC     TCC TTT GCG     GAT GGC CAG     CCT GCC GAG     CGC AGG GCC
 G   G   S       P   Q   G       S   F   A       D   G   Q       P   A   E       R   R   A 3141            3150            3159            3168            3177            3186
AGC AAT GAC     CAG CGT CCC     CAG GAG GTC     CCA GCA GAG     GCT CTG GCC     CCG GCC CCA
 S   N   D       Q   R   P       Q   E   V       P   A   E       A   L   A       P   A   P 3195            3204            3213            3222            3231            3240
GTG GAA GTC     CCA GCT CCA     GCA GCA GCC     TCA GCC TCA     GGC CCA GCG     AAG
 V   E   V       P   A   P       A   A   S       A   S   G       P   A   K 3249            3258            3267            3276            3285            3294
ACT CCG GCC     CCA GCA GAG     GCC CCT GCA     GCC TCA GCT     TTG GTC CCA     GAG ACG CCA
 T   P   A       P   A   E       A   P   A       A   S   A       L   V   P       E   T   P 3303            3312            3321            3330            3339            3348
GTG GAA GCT     CCA GCC CCA     CCC CCA GAG     GCC CCT GCC     CAG TAC CCG     AGT GAG
 V   E   A       P   A   P       P   P   E       A   P   A       Q   Y   P       S   E 3357            3366            3375            3384            3393            3402
CAC CTC ATC     CAG GCC ACC     TCG GAG GAG     AAT CAG ATC     CCC TCG CAC     TTG CCT GCC
 H   L   I       Q   A   T       S   E   E       N   Q   I       P   S   H       L   P   A
```

```
              3411         3420         3429         3438         3447         3456
       TGC CCG TCG CTC CGG CAC GTC GCC AGC CTG CGG CAC AGC GCC ATC ATC GAG CTC
        C   P   S   L   R   H   V   A   S   L   R   H   S   A   I   I   E   L 3465         3474         3483         3492         3501         3510
       TTC CAC AGC AGC ATT GCT GAG GTT GAA AAC GAG GAG CTG AGG CAC CTC ATG TGG
        F   H   S   S   I   A   E   V   E   N   E   E   L   R   H   L   M   W 3519         3528         3537         3546         3555         3564
       TCC GTG GTG TTC TAC CAG ACC CCA GGG CTG GAG GTG ACT GCC TGC GTG CTG
        S   V   V   F   Y   Q   T   P   G   L   E   V   T   A   C   V   L 3573         3582         3591         3600         3609         3618
       CTC TCC ACC AAG GCT GTG TAC TTT GTG CTC CAC GAC GGC CTC CGC TAC TTC
        L   S   T   K   A   V   Y   F   V   L   H   D   G   L   R   Y   F 3627         3636         3645         3654         3663         3672
       TCA GAG CCA CTG CAG GAT TTC TGG CAT CAG AAA AAC ACC GAC TAC AAC AAC AGC
        S   E   P   L   Q   D   F   W   H   Q   K   N   T   D   Y   N   N   S 3681         3690         3699         3708         3717         3726
       CCT TTC CAC ATC TCC CAG TGC TTC GTG CTA AAG CTT AGT GAC CTG CAG TCA GTC
        P   F   H   I   S   Q   C   F   V   L   K   L   S   D   L   Q   S   V 3735         3744         3753         3762         3771         3780
       AAT GTG GGG CTT TTC GAC CAG CAT TTC CGG CTG ACG GGT TCC ACC CCG ATG CAG
        N   V   G   L   F   D   Q   H   F   R   L   T   G   S   T   P   M   Q
```

FIGURE 1J

```
         3789          3798          3807          3816          3825          3834
GTG GTC ACG TGC TTG ACG GAC AGC TAC CTG ACG CAC TGC TTC CTC CAG CAC
 V   V   T   C   L   T   R   D   S   Y   L   T   H   C   F   L   Q   H 3843          3852          3861          3870          3879          3888
CTC ATG GTC CTG TCC TCT CTG GAA CGC ACG CCC TCG CCG GAG CCT GTT GAC
 L   M   V   L   S   S   L   E   R   T   P   S   P   E   P   V   D 3897          3906          3915          3924          3933          3942
AAG GAC TTC TAC TCC GAG TTT GGG AAC AAG ACC ACA GGG AAG ATG GAG AAC TAC
 K   D   F   Y   S   E   F   G   N   K   T   T   G   K   M   E   N   Y 3951          3960          3969          3978          3987          3996
GAG CTG ATC CAC TCT AGT CGC GTC AAG TTT ACC TAC CCC AGT GAG GAG GAG ATT
 E   L   I   H   S   S   R   V   K   F   T   Y   P   S   E   E   E   I 4005          4014          4023          4032          4041          4050
GGG GAC CTG ACG TTC ACT GTG GCC CAA AAG ATG GCT GAG CCA GAG AAG GCC CCA
 G   D   L   T   F   T   V   A   Q   K   M   A   E   P   E   K   A   P 4059          4068          4077          4086          4095          4104
GCC CTC AGC ATC CTG CTG TAC CTG TAC GTG CAG GCC TTC CAG GTG GGC ATG CCA CCC CCT
 A   L   S   I   L   L   Y   L   Y   V   Q   A   F   Q   V   G   M   P   P   P 4113          4122          4131          4140          4149          4158
GGG TGC TGC AGG GGC CCC CTG CGC CCC AAG ACA CTC CTG CTC ACC AGC TCC GAG
 G   C   C   R   G   P   L   R   P   K   T   L   L   L   T   S   S   E
```

FIGURE 1K

```
            4167            4176            4185            4194            4203            4212
ATC TTC CTC CTG GAT GAG GAC TGT GTC CAC TAC CCA CTG CCC GAG TTT GCC AAA
 I   F   L   L   D   E   D   C   V   H   Y   P   L   P   E   F   A   K 4221            4230            4239            4248            4257            4266
GAG CCG CCG CAG AGA GAC AGG TAC CGG CTG GAT GGC CGC CGC GTC CGG GAC
 E   P   P   Q   R   D   R   Y   R   L   D   D   G   R   R   V   R   D 4275            4284            4293            4302            4311            4320
CTG GAC CGA GTG CTC ATG GGC TAC CAG ACC TAC CCG CAG GCC CTC ACC CTC GTC
 L   D   R   V   L   M   G   Y   Q   T   Y   P   Q   A   L   T   L   V 4329            4338            4347            4356            4365            4374
TTC GAT GAC GTG CAA GGT CAT GAC CTC ATG GGC AGT GTC ACC CTG GAC CAC TTT
 F   D   D   V   Q   G   H   D   L   M   G   S   V   T   L   D   H   F 4383            4392            4401            4410            4419            4428
GGG GAG GTG CCA GGT GGC CCG GCT AGA GCC AGC CAG GGC CGT GAA GTC CAG TGG
 G   E   V   P   G   G   P   A   R   A   S   Q   G   R   E   V   Q   W 4437            4446            4455            4464            4473            4482
CAG GTG TTT GTC CCC AGT GCT GAG AGC AGA GAG AAG CTC ATC TCG CTG TTG GCT
 Q   V   F   V   P   S   A   E   S   R   E   K   L   I   S   L   L   A 4491            4500            4509            4518            4527            4536
CGC CAG TGG GAG GCC CTG TGT GGC CGT GAG CTG CCT GTC GAG CTC ACC GGC TAG
 R   Q   W   E   A   L   C   G   R   E   L   P   V   E   L   T   G
```

FIGURE 1L

```
     4545      4554      4563      4572      4581      4590
CCC AGG CCA CAG CCA GCC TGT CGT GTC CAG CCT GAC GCC TAC TGG GGC AGG GCA 4599      4608      4617      4626      4635      4644
GCA GGC TTT TGT GTT CTC TAA AAA TGT TTT ATC CTC CCT TTG GTA CCT TAA TTT 4653      4662      4671      4680      4689      4698
GAC TGT CCT CGC AGA GAA TGT GAA CAT GTG TGT GTG TTG TGT TAA TTC TTT CTC 4707      4716      4725      4734      4743      4752
ATG TTG GGA GTG AGA ATG CCG GGC CCC TCA GGG CTG TCG GTG TGC TGT CAG CCT 4761      4770      4779      4788      4797      4806
CCC ACA GGT GGT ACA GCC GTG CAC ACC AGT GTC GTG TCT GCT GTT GTG GGA CCG 4815      4824      4833      4842      4851      4860
TTG TTA ACA CGT GAC ACT GTG GGT CTG ACT TTC TCT TCT ACA CGT CCT TTC CTG 4869      4878      4887      4896      4905      4914
AAG TGT CGA GTC CAG TCC TTT GTT GCT GTT GCT GTT GCT GTT GCT GTT GCT GTT
```

FIGURE 1M

```
     4923      4932      4941      4950      4959      4968
GGC ATC TTG CTG CTA ATC CTG AGG CTG GTA GCA GAA TGC ACA TTG GAA GCT CCC 4977      4986      4995      5004      5013      5022
ACC CCA TAT TGT TCT TCA AAG TGG AGG TCT CCC CTG ATC CAG ACA AGT GGG AGA 5031      5040      5049      5058      5067      5076
GCC CGT GGG GGC AGG GGA CCT GGA GCT GCC AGC ACC AAG CGT GAT TCC TGC TGC 5085      5094      5103      5112      5121
CTG TAT TCT CTA TTC CAA TAA AGC AGA GTT TGA CAC CGT CAA AAA AAA AAA A 3'
```

```
211  FDLSIFKSLHQVEISHCDAKHIRGLVASKP   129581
 19  -GLTLVRPLRSVHL---------------   W43396

241  TLATLSVRFSATSMKEVLVPEASEFDEWEP   129581
 32  -----------------------------   W43396

271  EGTTLEGPVTAVIPTWQALTTLDLSHNSIS   129581
 32  -----------------------------   W43396

301  EIDESVKLIPKIEFLDLSHNGLLVVDNLQH   129581
 32  -----------------------------   W43396

331  LYNLVHLDLSYNKLSSLEGLHTKLGNIKTL   129581
 32  ---LDMSVQVIRPGEAFPTALADVR----   W43396

361  NLAGNLLESLSGLHKLYSLVNLDLRDNRIE   129581
 54  -----------------------------   W43396

391  QMEEVRSIGSLPCLEHVSLLNNPLSIIPDY   129581
 54  -----------------------------   W43396

421  RTKVLAQFGERASEVCLDDTVTTEKELDTV   129581
 54  -----------------------------   W43396
```

| | | |
|---|---|---|
| 691 | EWALGADEDFLLEHIRILKVLWCFLIHVQG | 129581 |
| 279 | EWALGADEDFLLEHIRILKVLWCFLIHVQG | W43396 |
| 721 | SIRQFAACLVLTDFGIAVFEIPHQESRGSS | 129581 |
| 309 | SIRQFAACLVLTDFGIAVFEIPHQESWGSS | W43396 |
| 751 | QHILSSLRFVFCFPHGDLTEFGFLMPELCL | 129581 |
| 339 | QHILSSLRFVFCFRMATSPS---LASSC-  | W43396 |
| 781 | VLKVRHSENTLFIISDAANLHEFHADLRSC | 129581 |
| 364 | ----------------------- --WSC  | W43396 |
| 811 | FAPQHMAMLCSPILYGSHTSLQEFLRQLLT | 129581 |
| 367 | ----VWCSR--YGT-------VRTRSS    | W43396 |
| 841 | FYKVAGGCQERSQGCFPVYLVYSDKRMVQT | 129581 |
| 381 | LSWTPPTCTSSTWTC--------AHALHP  | W43396 |
| 871 | AAGDYSGNIEWASCTLCSAVRRSCCAPSEA | 129581 |
| 402 | ST-------WP-----------CCVA---  | W43396 |

SEQUENCE LISTING

<160> NUMBER OF SEQ ID NOS: 47

<210> SEQ ID NO 1
<211> LENGTH: 5128
<212> TYPE: DNA
<213> ORGANISM: Homo sapiens
<220> FEATURE:
<221> NAME/KEY:
<223> OTHER INFORMATION: 129581CB1
<300> PUBLICATION INFORMATION:

<400> SEQUENCE: 1

| | | | | | |
|---|---|---|---|---|---|
| ggtggcggcg | gagacccgaa | catggcgacc | gcgcgcacct | tcgggcccga | gcgggaagcc | 60 |
| gagccggcca | aggaagcgcg | cgtcgtgggc | tcggagcttg | tggacactta | tacggtttac | 120 |
| atcatccagg | tcactgatgg | cagccatgag | tggacagtaa | agcaccgcta | cagcgacttc | 180 |
| catgacctgc | atgaaaagct | cgttgcagag | agaaagattg | ataaaaacct | gcttccgccc | 240 |
| aaaaagataa | ttgggaaaaa | ctcaagaagc | ttggtggaga | agaggagaa | ggatctggag | 300 |
| gtctacctcc | agaagctcct | ggctgccttc | cctggcgtga | ccccagagt | actggcccac | 360 |
| ttcttgcatt | ttcacttcta | tgagataaat | ggcatcaccg | cggcactggc | tgaagagctc | 420 |
| tttgagaaag | gagaacagct | cctgggggcc | ggcgaggtct | ttgccattgg | accctgcag | 480 |
| ctgtatgccg | tcacggagca | gctgcagcag | ggaaagccca | cgtgcgccag | tggggatgcc | 540 |
| aagaccgacc | tcgggcacat | cctggacttc | acctgtcgcc | ttaagtacct | taaggtttct | 600 |
| ggcacagaag | gacctttgg | gaccagcaac | attcaggagc | agctcctgcc | gttcgaccta | 660 |
| tcaatattca | agtccctgca | tcaggtggag | ataagtcact | gtgatgctaa | gcacatcaga | 720 |
| gggctggtcg | catcgaagcc | caccttagcc | acgctgagtg | tccgcttctc | agcaacctcg | 780 |
| atgaaggaag | tccttgttcc | tgaagcctca | gaatttgatg | agtgggagcc | tgaaggcaca | 840 |
| accctagaag | gccctgtgac | tgccgtcatc | cccacttggc | aggcattgac | cacgcttgac | 900 |
| ctgagccaca | cagcatctc | cgagatcgac | gagtctgtga | aactgatccc | aaagattgag | 960 |
| ttcctggacc | tgagtcacaa | tggattgctg | gttgtggaca | atctgcagca | cctgtataac | 1020 |
| cttgtgcatc | tggacctgtc | ctacaacaag | ctctcctcct | tggaagggct | tcacaccaag | 1080 |
| ctggggaaca | tcaagacctt | aaacctggca | ggcaacctcc | tagagagtct | gagtggcctg | 1140 |
| cacaagctct | actcactggt | caacctggat | ctccgggaca | acaggatcga | acagatggag | 1200 |
| gaggtccgga | gcataggcag | cctcccgtgt | ctggagcacg | tgtctctgct | gaacaaccct | 1260 |
| ctgagcatca | tccccgacta | ccggaccaag | gtgctggctc | agttcggaga | gagggcctca | 1320 |
| gaggtctgtc | tggatgacac | agtgaccaca | gagaaggagc | tggacactgt | ggaagtgctg | 1380 |
| aaagcaattc | agaaagccaa | ggaggtcaag | tccaaactga | gcaacccaga | gaagaaggt | 1440 |
| ggtgaagact | cccggctctc | agctgccccc | tgcatcagac | ccagcagctc | ccctcccact | 1500 |
| gtggctcccg | catctgcctc | cctgcccag | cccatcctct | ctaaccaagg | aatcatgttc | 1560 |
| gttcaggagg | aggccctggc | cagcagcctc | tcgtccactg | acagtctgac | tcccgagcac | 1620 |
| cagcccattg | cccagggatg | ttctgattcc | ttggagtcca | tccctgcggg | acaggcagct | 1680 |
| tccgatgatt | taagggacgt | gccaggagct | gttggtggtg | caagcccaga | acatgccgag | 1740 |
| ccggaggtcc | agtggtgcc | ggggtctggc | cagatcatct | tcctgccctt | cacctgcatt | 1800 |
| ggctacacgg | ccaccaatca | ggacttcatc | cagcgcctga | gcacactgat | ccggcaggcc | 1860 |
| atcgagcggc | agctgcctgc | ctggatcgag | gctgccaacc | agcgggagga | gggccagggt | 1920 |

-continued

```
gaacagggcg aggaggagga tgaggaggag gaagaagagg aggacgtggc tgagaaccgc    1980
tactttgaaa tggggccccc agacgtggag gaggaggagg gaggaggcca gggggaggaa    2040
gaggaggagg aagaggagga tgaagaggcc gaggaggagc gcctggctct ggaatgggcc    2100
ctgggcgcgg acgaggactt cctgctggag cacatccgca tcctcaaggt gctgtggtgc    2160
ttcctgatcc atgtgcaggg cagtatccgc cagttcgccg cctgccttgt gctcaccgac    2220
ttcggcatcg cagtcttcga gatcccgcac caggagtctc ggggcagcag ccagcacatc    2280
ctctcctccc tgcgctttgt cttttgcttc ccgcatggcc acctcaccga gtttggcttc    2340
ctcatgccgg agctgtgtct ggtgctcaag gtacggcaca gtgagaacac gctcttcatt    2400
atctcggacg ccgccaacct gcacgagttc cacgcggacc tgcgctcatg ctttgcaccc    2460
cagcacatgg ccatgctgtg tagccccatc ctctacggca gccacaccag cctgcaggag    2520
ttcctgcgcc agctgctcac cttctacaag gtggctggcg gctgccagga gcgcagccag    2580
ggctgcttcc ccgtctacct ggtctacagt gacaagcgca tggtgcagac ggccgccggg    2640
gactactcag gcaacatcga gtgggccagc tgcacactct gttcagccgt gcggcgctcc    2700
tgctgcgcgc cctctgaggc cgtcaagtcc gccgccatcc cctactggct gttgctcacg    2760
ccccagcacc tcaacgtcat caaggccgac ttcaacccca tgcccaaccg tgcaccccac    2820
aactgtcgca accgcaacag cttcaagctc agccgtgtgc cgctctccac cgtgctgctg    2880
gaccccacac gcagctgtac ccagcctcgg ggcgcctttg ctgatggcca cgtgctagag    2940
ctgctcgtgg ggtaccgctt tgtcactgcc atcttcgtgc tgccccacga gaagttccac    3000
ttcctgcgcg tctacaacca gctgcgggcc tcgctgcagg acctgaagac tgtggtcatc    3060
gccaagaccc ccgggacggg aggcagcccc cagggctcct tgcggatgg ccagcctgcc    3120 gagcgcaggg ccagcaatga ccagcgtccc caggaggtcc cagcagaggc tctggccccg    3180
gccccagtgg aagtcccagc tccagcccct gcagcagcct cagcctcagg cccagcgaag    3240
actccggccc cagcagaggc ctcaacttca gctttggtcc cagaggagac gccagtggaa    3300
gctccagccc caccccagc cgaggcccct gcccagtacc cgagtgagca cctcatccag    3360
gccacctcgg aggagaatca gatcccctcg cacttgcctg cctgcccgtc gctccggcac    3420
gtcgccagcc tgcggggcag cgccatcatc gagctcttcc acagcagcat tgctgaggtt    3480
gaaaacgagg agctgaggca cctcatgtgg tcctcggtgg tgttctacca gacccccaggg    3540 ctggaggtga ctgcctgcgt gctgctctcc accaaggctg tgtactttgt gctccacgac    3600
ggcctccgcc gctacttctc agagccactg caggatttct ggcatcagaa aaacaccgac    3660
tacaacaaca gcccttttcca catctcccag tgcttcgtgc taaagcttag tgacctgcag    3720
tcagtcaatg tggggctttt cgaccagcat ttccggctga cgggttccac cccgatgcag    3780
gtggtcacgt gcttgacgcg ggacagctac ctgacgcact gcttcctcca gcacctcatg    3840
gtcgtgctgt cctctctgga acgcacgccc tcgccggagc tgttgacaa ggacttctac    3900 tccgagtttg gaacaagac cacagggaag atggagaact acgagctgat ccactctagt    3960
cgcgtcaagt ttacctaccc cagtgaggag gagattgggg acctgacgtt cactgtggcc    4020
caaaagatgg ctgagccaga gaaggcccca gccctcagca tcctgctgta cgtgcaggcc    4080
ttccaggtgg gcatgccacc ccctgggtgc tgcagggcc cctgcgcccc aagacactc    4140 ctgctcacca gctccgagat cttcctcctg gatgaggact gtgtccacta cccactgccc    4200
gagtttgcca aagagccgcc gcagagagac aggtaccggc tggacgatgg ccgccgcgtc    4260
```

-continued

```
cgggacctgg accgagtgct catgggctac cagacctacc cgcaggccct caccctcgtc    4320
ttcgatgacg tgcaaggtca tgacctcatg ggcagtgtca ccctggacca ctttggggag    4380
gtgccaggtg gcccggctag agccagccag ggccgtgaag tccagtggca ggtgtttgtc    4440
cccagtgctg agagcagaga gaagctcatc tcgctgttgg ctcgccagtg ggaggccctg    4500
tgtggccgtg agctgcctgt cgagctcacc ggctagccca ggccacagcc agcctgtcgt    4560
gtccagcctg acgcctactg gggcagggca gcaggctttt gtgttctcta aaaatgtttt    4620
atcctccctt tggtacctta atttgactgt cctcgcagag aatgtgaaca tgtgtgtgtg    4680
ttgtgttaat tctttctcat gttgggagtg agaatgccgg gcccctcagg gctgtcggtg    4740
tgctgtcagc ctcccacagg tggtacagcc gtgcacacca gtgtcgtgtc tgctgttgtg    4800
ggaccgttgt taacacgtga cactgtgggt ctgactttct cttctacacg tcctttcctg    4860
aagtgtcgag tccagtcctt tgttgctgtt gctgttgctg ttgctgttgc tgttggcatc    4920
ttgctgctaa tcctgaggct ggtagcagaa tgcacattgg aagctcccac cccatattgt    4980
tcttcaaagt ggaggtctcc cctgatccag acaagtggga gagcccgtgg gggcagggga    5040
cctggagctg ccagcaccaa gcgtgattcc tgctgcctgt attctctatt ccaataaagc    5100
agagtttgac accgtcaaaa aaaaaaaa                                       5128
```

<210> SEQ ID NO 2
<211> LENGTH: 1504
<212> TYPE: PRT
<213> ORGANISM: Homo sapiens
<220> FEATURE:
<221> NAME/KEY:
<223> OTHER INFORMATION: 129581CD1
<300> PUBLICATION INFORMATION:

<400> SEQUENCE: 2

```
Met Ala Thr Ala Arg Thr Phe Gly Pro Glu Arg Glu Ala Glu Pro
  1               5                  10                  15

Ala Lys Glu Ala Arg Val Val Gly Ser Glu Leu Val Asp Thr Tyr
                 20                  25                  30

Thr Val Tyr Ile Ile Gln Val Thr Asp Gly Ser His Glu Trp Thr
                 35                  40                  45

Val Lys His Arg Tyr Ser Asp Phe His Asp Leu His Glu Lys Leu
                 50                  55                  60

Val Ala Glu Arg Lys Ile Asp Lys Asn Leu Leu Pro Pro Lys Lys
                 65                  70                  75

Ile Ile Gly Lys Asn Ser Arg Ser Leu Val Glu Lys Arg Glu Lys
                 80                  85                  90

Asp Leu Glu Val Tyr Leu Gln Lys Leu Leu Ala Ala Phe Pro Gly
                 95                 100                 105

Val Thr Pro Arg Val Leu Ala His Phe Leu His Phe His Phe Tyr
                110                 115                 120

Glu Ile Asn Gly Ile Thr Ala Ala Leu Ala Glu Glu Leu Phe Glu
                125                 130                 135

Lys Gly Glu Gln Leu Leu Gly Ala Gly Glu Val Phe Ala Ile Gly
                140                 145                 150

Pro Leu Gln Leu Tyr Ala Val Thr Glu Gln Leu Gln Gln Gly Lys
                155                 160                 165

Pro Thr Cys Ala Ser Gly Asp Ala Lys Thr Asp Leu Gly His Ile
                170                 175                 180

Leu Asp Phe Thr Cys Arg Leu Lys Tyr Leu Lys Val Ser Gly Thr
```

-continued

```
                    185                 190                 195
Glu Gly Pro Phe Gly Thr Ser Asn Ile Gln Glu Gln Leu Leu Pro
                200                 205                 210
Phe Asp Leu Ser Ile Phe Lys Ser Leu His Gln Val Glu Ile Ser
                215                 220                 225
His Cys Asp Ala Lys His Ile Arg Gly Leu Val Ala Ser Lys Pro
                230                 235                 240
Thr Leu Ala Thr Leu Ser Val Arg Phe Ser Ala Thr Ser Met Lys
                245                 250                 255
Glu Val Leu Val Pro Glu Ala Ser Glu Phe Asp Glu Trp Glu Pro
                260                 265                 270
Glu Gly Thr Thr Leu Glu Gly Pro Val Thr Ala Val Ile Pro Thr
                275                 280                 285
Trp Gln Ala Leu Thr Thr Leu Asp Leu Ser His Asn Ser Ile Ser
                290                 295                 300
Glu Ile Asp Glu Ser Val Lys Leu Ile Pro Lys Ile Glu Phe Leu
                305                 310                 315
Asp Leu Ser His Asn Gly Leu Leu Val Val Asp Asn Leu Gln His
                320                 325                 330
Leu Tyr Asn Leu Val His Leu Asp Leu Ser Tyr Asn Lys Leu Ser
                335                 340                 345
Ser Leu Glu Gly Leu His Thr Lys Leu Gly Asn Ile Lys Thr Leu
                350                 355                 360
Asn Leu Ala Gly Asn Leu Leu Glu Ser Leu Ser Gly Leu His Lys
                365                 370                 375
Leu Tyr Ser Leu Val Asn Leu Asp Leu Arg Asp Asn Arg Ile Glu
                380                 385                 390
Gln Met Glu Glu Val Arg Ser Ile Gly Ser Leu Pro Cys Leu Glu
                395                 400                 405
His Val Ser Leu Leu Asn Asn Pro Leu Ser Ile Ile Pro Asp Tyr
                410                 415                 420
Arg Thr Lys Val Leu Ala Gln Phe Gly Glu Arg Ala Ser Glu Val
                425                 430                 435
Cys Leu Asp Asp Thr Val Thr Thr Glu Lys Glu Leu Asp Thr Val
                440                 445                 450
Glu Val Leu Lys Ala Ile Gln Lys Ala Lys Glu Val Lys Ser Lys
                455                 460                 465
Leu Ser Asn Pro Glu Lys Lys Gly Gly Glu Asp Ser Arg Leu Ser
                470                 475                 480
Ala Ala Pro Cys Ile Arg Pro Ser Ser Ser Pro Thr Val Ala
                485                 490                 495
Pro Ala Ser Ala Ser Leu Pro Gln Pro Ile Leu Ser Asn Gln Gly
                500                 505                 510
Ile Met Phe Val Gln Glu Glu Ala Leu Ala Ser Ser Leu Ser Ser
                515                 520                 525
Thr Asp Ser Leu Thr Pro Glu His Gln Pro Ile Ala Gln Gly Cys
                530                 535                 540
Ser Asp Ser Leu Glu Ser Ile Pro Ala Gly Gln Ala Ala Ser Asp
                545                 550                 555
Asp Leu Arg Asp Val Pro Gly Ala Val Gly Ala Ser Pro Glu
                560                 565                 570
His Ala Glu Pro Glu Val Gln Val Val Pro Gly Ser Gly Gln Ile
                575                 580                 585
```

-continued

```
Ile Phe Leu Pro Phe Thr Cys Ile Gly Tyr Thr Ala Thr Asn Gln
            590                 595                 600

Asp Phe Ile Gln Arg Leu Ser Thr Leu Ile Arg Gln Ala Ile Glu
            605                 610                 615

Arg Gln Leu Pro Ala Trp Ile Glu Ala Asn Gln Arg Glu Glu
            620                 625                 630

Gly Gln Gly Glu Gln Gly Glu Glu Glu Asp Glu Glu Glu Glu Glu
            635                 640                 645

Glu Glu Asp Val Ala Glu Asn Arg Tyr Phe Glu Met Gly Pro Pro
            650                 655                 660

Asp Val Glu Glu Glu Gly Gly Gly Gln Gly Glu Glu Glu
            665                 670                 675

Glu Glu Glu Glu Asp Glu Glu Ala Glu Glu Arg Leu Ala Leu
            680                 685                 690

Glu Trp Ala Leu Gly Ala Asp Glu Asp Phe Leu Leu Glu His Ile
            695                 700                 705

Arg Ile Leu Lys Val Leu Trp Cys Phe Leu Ile His Val Gln Gly
            710                 715                 720

Ser Ile Arg Gln Phe Ala Ala Cys Leu Val Leu Thr Asp Phe Gly
            725                 730                 735

Ile Ala Val Phe Glu Ile Pro His Gln Glu Ser Arg Gly Ser Ser
            740                 745                 750

Gln His Ile Leu Ser Ser Leu Arg Phe Val Phe Cys Phe Pro His
            755                 760                 765

Gly Asp Leu Thr Glu Phe Gly Phe Leu Met Pro Glu Leu Cys Leu
            770                 775                 780

Val Leu Lys Val Arg His Ser Glu Asn Thr Leu Phe Ile Ile Ser
            785                 790                 795

Asp Ala Ala Asn Leu His Glu Phe His Ala Asp Leu Arg Ser Cys
            800                 805                 810

Phe Ala Pro Gln His Met Ala Met Leu Cys Ser Pro Ile Leu Tyr
            815                 820                 825

Gly Ser His Thr Ser Leu Gln Glu Phe Leu Arg Gln Leu Leu Thr
            830                 835                 840

Phe Tyr Lys Val Ala Gly Gly Cys Gln Glu Arg Ser Gln Gly Cys
            845                 850                 855

Phe Pro Val Tyr Leu Val Tyr Ser Asp Lys Arg Met Val Gln Thr
            860                 865                 870

Ala Ala Gly Asp Tyr Ser Gly Asn Ile Glu Trp Ala Ser Cys Thr
            875                 880                 885

Leu Cys Ser Ala Val Arg Arg Ser Cys Cys Ala Pro Ser Glu Ala
            890                 895                 900

Val Lys Ser Ala Ala Ile Pro Tyr Trp Leu Leu Thr Pro Gln
            905                 910                 915

His Leu Asn Val Ile Lys Ala Asp Phe Asn Pro Met Pro Asn Arg
            920                 925                 930

Gly Thr His Asn Cys Arg Asn Arg Asn Ser Phe Lys Leu Ser Arg
            935                 940                 945

Val Pro Leu Ser Thr Val Leu Leu Asp Pro Thr Arg Ser Cys Thr
            950                 955                 960

Gln Pro Arg Gly Ala Phe Ala Asp Gly His Val Leu Glu Leu Leu
            965                 970                 975
```

-continued

```
Val Gly Tyr Arg Phe Val Thr Ala Ile Phe Val Leu Pro His Glu
            980                 985                 990

Lys Phe His Phe Leu Arg Val Tyr Asn Gln Leu Arg Ala Ser Leu
            995                1000                1005

Gln Asp Leu Lys Thr Val Val Ile Ala Lys Thr Pro Gly Thr Gly
           1010                1015                1020

Gly Ser Pro Gln Gly Ser Phe Ala Asp Gly Gln Pro Ala Glu Arg
           1025                1030                1035

Arg Ala Ser Asn Asp Gln Arg Pro Gln Glu Val Pro Ala Glu Ala
           1040                1045                1050

Leu Ala Pro Ala Pro Val Glu Val Pro Ala Pro Ala Pro Ala Ala
           1055                1060                1065

Ala Ser Ala Ser Gly Pro Ala Lys Thr Pro Ala Pro Ala Glu Ala
           1070                1075                1080

Ser Thr Ser Ala Leu Val Pro Glu Glu Thr Pro Val Glu Ala Pro
           1085                1090                1095

Ala Pro Pro Ala Glu Ala Pro Ala Gln Tyr Pro Ser Glu His
           1100                1105                1110

Leu Ile Gln Ala Thr Ser Glu Glu Asn Gln Ile Pro Ser His Leu
           1115                1120                1125

Pro Ala Cys Pro Ser Leu Arg His Val Ala Ser Leu Arg Gly Ser
           1130                1135                1140

Ala Ile Ile Glu Leu Phe His Ser Ser Ile Ala Glu Val Glu Asn
           1145                1150                1155

Glu Glu Leu Arg His Leu Met Trp Ser Ser Val Val Phe Tyr Gln
           1160                1165                1170

Thr Pro Gly Leu Glu Val Thr Ala Cys Val Leu Leu Ser Thr Lys
           1175                1180                1185

Ala Val Tyr Phe Val Leu His Asp Gly Leu Arg Arg Tyr Phe Ser
           1190                1195                1200

Glu Pro Leu Gln Asp Phe Trp His Gln Lys Asn Thr Asp Tyr Asn
           1205                1210                1215

Asn Ser Pro Phe His Ile Ser Gln Cys Phe Val Leu Lys Leu Ser
           1220                1225                1230

Asp Leu Gln Ser Val Asn Val Gly Leu Phe Asp Gln His Phe Arg
           1235                1240                1245

Leu Thr Gly Ser Thr Pro Met Gln Val Val Thr Cys Leu Thr Arg
           1250                1255                1260

Asp Ser Tyr Leu Thr His Cys Phe Leu Gln His Leu Met Val Val
           1265                1270                1275

Leu Ser Ser Leu Glu Arg Thr Pro Ser Pro Glu Pro Val Asp Lys
           1280                1285                1290

Asp Phe Tyr Ser Glu Phe Gly Asn Lys Thr Thr Gly Lys Met Glu
           1295                1300                1305

Asn Tyr Glu Leu Ile His Ser Ser Arg Val Lys Phe Thr Tyr Pro
           1310                1315                1320

Ser Glu Glu Glu Ile Gly Asp Leu Thr Phe Thr Val Ala Gln Lys
           1325                1330                1335

Met Ala Glu Pro Glu Lys Ala Pro Ala Leu Ser Ile Leu Leu Tyr
           1340                1345                1350

Val Gln Ala Phe Gln Val Gly Met Pro Pro Pro Gly Cys Cys Arg
           1355                1360                1365

Gly Pro Leu Arg Pro Lys Thr Leu Leu Leu Thr Ser Ser Glu Ile
```

```
                          1370            1375            1380
     Phe Leu Leu Asp Glu Asp Cys Val His Tyr Pro Leu Pro Glu Phe
                      1385            1390            1395
     Ala Lys Glu Pro Pro Gln Arg Asp Arg Tyr Arg Leu Asp Asp Gly
                  1400            1405            1410
     Arg Arg Val Arg Asp Leu Asp Arg Val Leu Met Gly Tyr Gln Thr
              1415            1420            1425
     Tyr Pro Gln Ala Leu Thr Leu Val Phe Asp Asp Val Gln Gly His
          1430            1435            1440
     Asp Leu Met Gly Ser Val Thr Leu Asp His Phe Gly Glu Val Pro
      1445            1450            1455
     Gly Gly Pro Ala Arg Ala Ser Gln Gly Arg Glu Val Gln Trp Gln
  1460            1465            1470
     Val Phe Val Pro Ser Ala Glu Ser Arg Glu Lys Leu Ile Ser Leu
          1475            1480            1485
     Leu Ala Arg Gln Trp Glu Ala Leu Cys Gly Arg Glu Leu Pro Val
          1490            1495            1500
     Glu Leu Thr Gly

<210> SEQ ID NO 3
<211> LENGTH: 256
<212> TYPE: DNA
<213> ORGANISM: Homo sapiens
<220> FEATURE:
<221> NAME/KEY:
<223> OTHER INFORMATION: 3276916H1
<300> PUBLICATION INFORMATION:

<400> SEQUENCE: 3
gcggcggtgg cggcggagac ccgaacatgg cgaccgcgcg caccttcggg cccgagcggg     60
aagccgagcc ggccaaggaa gcgcgcgtcg tgggctcgga gcttgtggac acttatacgg    120
tttacatcat ccaggtcact gatggcagcc atgagtggac agtaaagcac cgctacagcg    180
acttccatga cctgcatgaa aagctcgttg cagagagaaa gattgataaa aacctgcttc    240
cgcccaaaaa gataat                                                    256

<210> SEQ ID NO 4
<211> LENGTH: 208
<212> TYPE: DNA
<213> ORGANISM: Homo sapiens
<220> FEATURE:
<221> NAME/KEY: unsure
<222> LOCATION: 9
<223> OTHER INFORMATION: a or g or c or t, unknown, or other
<220> FEATURE:
<221> NAME/KEY:
<223> OTHER INFORMATION: 2431638H1
<300> PUBLICATION INFORMATION:

<400> SEQUENCE: 4
gacccgaana tggcgaccgc gcgcaccttc gggcccgagc gggaagccga gccggccaag     60
gaagcgcgcg tcgtgggctc ggagcttgtg gacacttata cggtttacat catccaggtc    120
actgatggca gccatgagtg gacagtaaag caccgctaca gcgacttcca tgacctgcat    180
gaaaagctcg ttgcagagag aaagattg                                       208

<210> SEQ ID NO 5
<211> LENGTH: 493
<212> TYPE: DNA
<213> ORGANISM: Homo sapiens
```

```
<220> FEATURE:
<221> NAME/KEY: unsure
<222> LOCATION: 436
<223> OTHER INFORMATION: a or g or c or t, unknown, or other
<220> FEATURE:
<221> NAME/KEY:
<223> OTHER INFORMATION: 2263366X12F1
<300> PUBLICATION INFORMATION:

<400> SEQUENCE: 5
agccgaacat ggcgaccacg cgcaccttcg ggcccgagcg ggaagccgag ccggccaagg      60
gagcgcgcgt cgtgggctcg gagcttgtgg acacttatac ggtttacatc atccaggtca     120
ctgatggcag ccatgagtgg acagtaaagc accgctacag cgacttccat gacctgcatg     180
aaaagctcgt tgcagagaga aagattgata aaacccgct tccgcccaaa aagataattg      240
ggaaaaactc aagaagcttg gtggagaaga gggagaagga tctggaggtc tacctccaga     300
agctcctggc tgccttccct ggcgtgaccc ccagagtact ggcccacttc ttgcattttc     360
acttctatga gataaatggc atcaccgcgg cactggctga agagctcttt gagaaaggag     420
aacagctcct gggggncggc gaggtctttg ccattgggac ccctgcagct gtatgnccgt     480
cacggagcag ctg                                                       493

<210> SEQ ID NO 6
<211> LENGTH: 557
<212> TYPE: DNA
<213> ORGANISM: Homo sapiens
<220> FEATURE:
<221> NAME/KEY: unsure
<222> LOCATION:
<221> NAME/KEY: unsure
<222> LOCATION: 514,523,538,546
<223> OTHER INFORMATION: a or g or c or t, unknown, or other
<220> FEATURE:
<221> NAME/KEY:
<223> OTHER INFORMATION: 2526601F6
<300> PUBLICATION INFORMATION:

<400> SEQUENCE: 6
tggcgaccgc gcgcaccttc gggcccgagc gggaagccga gccggccaag gaagcgcgcg      60
tcgtgggctc ggagcttgtg gacacttata cggtttacat catccaggtc actgatggca     120
gccatgagtg gacagtaaag caccgctaca gcgacttcca tgacctgcnt gaaaagctcg     180
ttgcagagag aaagattgat aaaaacctgc ttccgcccaa aaagataatt gggaaaaact     240
caagaagctt ggtggagaag agggagaagg atctggangt ctactccaga agctcctggg     300
ctgcttncct ggcgtgaccc cccagagtac nggcccacnt cttgcatttc acttctatga     360
gataaatggc atcacgcggn actggctgaa agagctcctt tgaggaaagg nngaacaagt     420
ncttgggggg ccngggcnaa gggtcttttg nccaattggg aaccccctgg caagattgna     480
atgccngttn acgggnngca agctttcaag canngggaa aagncccccac cgttgcgncc     540 aaattnggg ggaatgc                                                    557

<210> SEQ ID NO 7
<211> LENGTH: 269
<212> TYPE: DNA
<213> ORGANISM: Homo sapiens
<220> FEATURE:
<221> NAME/KEY: unsure
<222> LOCATION: 205
<223> OTHER INFORMATION: a or g or c or t, unknown, or other
<220> FEATURE:
<221> NAME/KEY:
<223> OTHER INFORMATION: 4031726H1
```

```
<300> PUBLICATION INFORMATION:

<400> SEQUENCE: 7
atctggaggt ctacctccag aagctcctgg ctgccttccc tggcgtgacc cccagagtac      60
tggcccactt cttgcatttt cacttctatg agataaatgg catcaccgcg gcactggctg     120
aagagctctt tgagaaagga gaacagctcc tgggggccgg cgaggtcttt gccattggac     180
ccctgcagct gtatgccgtc acggngcagc tgcagcaggg aaagcccacg tgcgccagtg     240
gggatgccaa gaccgacctc gggcacatc                                       269

<210> SEQ ID NO 8
<211> LENGTH: 532
<212> TYPE: DNA
<213> ORGANISM: Homo sapiens
<220> FEATURE:
<221> NAME/KEY: unsure
<222> LOCATION: 500,516,520,523
<223> OTHER INFORMATION: a or g or c or t, unknown, or other
<220> FEATURE:
<221> NAME/KEY:
<223> OTHER INFORMATION: 4014626F6
<300> PUBLICATION INFORMATION:

<400> SEQUENCE: 8
ggtcggtctt ggcatcctgg acttcacctg tcgccttaag taccttaagg tttctggcac      60
agaaggacct tttgggacca gcaacattca ggagcagctc ctgccgttcg acctatcaat     120
attcaagtcc ctgcatcagg tggagataag tcactgtgat gctaagcaca tcagagggct     180
ggtcgcatcg aagcccacct tagccacgct gagtgtccgc ttctcagcaa cctcgatgaa     240
ggaagtcctt gttcctgaag cctcagaatt tgatgagtgg gagcctgaag gcacaaccct     300
agaaggccct gtgactgccg tcatccccac ttggcaggca ttgaccacgc ttgacctgag     360
ccacaacagc atctccgaga tcgacgagtc tgtgaaactg atcccaaaga ttgagttcct     420
ggacctgagt cacaatggat tgctggttgt ggacaatctg cagcacctgt ataaccttgt     480
gcatctggac tgtctacaan aaagctctcc tccttngaan ggnttcacac cc             532

<210> SEQ ID NO 9
<211> LENGTH: 488
<212> TYPE: DNA
<213> ORGANISM: Homo sapiens
<220> FEATURE:
<221> NAME/KEY: unsure
<222> LOCATION: 475
<223> OTHER INFORMATION: a or g or c or t, unknown, or other
<220> FEATURE:
<221> NAME/KEY:
<223> OTHER INFORMATION: 2263366X16F1
<300> PUBLICATION INFORMATION:

<400> SEQUENCE: 9
agcagcatct ccgagatcga cgagtctgtg aaatgatccc aaagattgag ttcctggacc      60
tgagtcacaa tggattgctg gttgtggaca atctgcagca cctgtataac cttgtgcatc     120
tggacctgtc ctacaacaag ctctcctcct tggaagggct tcacaccaag ctggggaaca     180
tcaagacctt aaacctggca ggcaacctcc tagagagtct gagtggcctg cacaagctct     240
actcactggt caacctggat ctccgggaca acaggatcga acagatggag gaggtccgga     300
gcataggcag cctcccgtgt ctggagcacg tgtctctgct gaacaaccct ctgagcatca     360
tccccgacta ccggaccaag gtgctggctc agttcggaga gagggcctca gaggtctgtc     420
tggatgacac agtgaccaca gagaaggagc tggacactgt ggaagtgctg aaaanaattt     480
``` cagaaagc                                                                                    488

<210> SEQ ID NO 10
<211> LENGTH: 586
<212> TYPE: DNA
<213> ORGANISM: Homo sapiens
<220> FEATURE:
<221> NAME/KEY: unsure
<222> LOCATION: 499,509,540,565,570,572,576,580,581,582,585
<223> OTHER INFORMATION: a or g or c or t, unknown, or other
<220> FEATURE:
<221> NAME/KEY:
<223> OTHER INFORMATION: 2488189F6
<300> PUBLICATION INFORMATION:

<400> SEQUENCE: 10

```
caaagattga gttcctggac ctgagtcaca atggattgct ggttgtggac aatctgcagc        60
acctgtatat ccttgtgcat ctggacctgt cctacaacaa gctctcctcc ttggaagggc       120
ttcacaccaa gctggggaac atcaagacct taaacctggc aggcaacctc ctagagagtc       180
tgagtggcct gcacaagctc tactcactgg tcaacctgga tctccgggac aacaggatcg       240
aacagatgga ggaggtccgg agcataggca gcctcccgtg tctggagcac gtgtctctgc       300
tgaacaaccc tctgagcatc atccccgact accggaccaa ggtgctggct cagttcggag       360
agagggcctc agaggtctgt ctggatgaca cagtgaccac agagaaggag ctggacactg       420
tggaagtgct gaaagaattc agaaagccaa ggaggtcaag tccaaactga gcaacccaga       480 gaaaaaggg tggtaaaana ctcccgggnt ttaagttggc ccctgaaat tagaaccccn        540 gaagttcccc ttcccaattg ggggnccccn gnattntgcn nnccnt                      586
```

<210> SEQ ID NO 11
<211> LENGTH: 634
<212> TYPE: DNA
<213> ORGANISM: Homo sapiens
<220> FEATURE:
<221> NAME/KEY: unsure
<222> LOCATION: 626,633
<223> OTHER INFORMATION: a or g or c or t, unknown, or other
<220> FEATURE:
<221> NAME/KEY:
<223> OTHER INFORMATION: 4014626T6
<300> PUBLICATION INFORMATION:

<400> SEQUENCE: 11

```
tggggaacat caagacctta aacttggcag gcaacctcct agagagtctg agtggcctgc        60
acaactctac tcactggtca acctggatct ccgggacaac aggatcgaac agatggagga       120
ggtccggagc ataggcagcc tcccgtgtct ggagcacgtg tctctgctga acaaccctct       180
gagcatcatc cccgactacc ggaccaaggt gctggctcag ttcggagaga gggcctcaga       240
ggtctgtctg gatgacacag tgaccacaga aggagctg gacactgtgg aagtgctgaa       300
agcaattcag aaagccaagg aggtcaagtc caaactgagc aacccagaga agaagggtgg       360
tgaagactcc cggctctcag ctgccccctg catctgcttc tcaaggccag ggacacagcc       420
agtgaagagc aggccctgga tgggtgggga tgcaccatgt ccccaggctg cagctgcagg       480 cagccccca cattgtcgga gaagcctctg caccagctca gcccctcct cactcccctt       540 gtgccctggg gacactctgc agaggggcac tctgcagtct gtccccgcca tcgctggact       600
tctggacatg gcctccagag ggcacntctt aant                                    634
```

<210> SEQ ID NO 12

```
<211> LENGTH: 259
<212> TYPE: DNA
<213> ORGANISM: Homo sapiens
<220> FEATURE:
<221> NAME/KEY:
<223> OTHER INFORMATION: 2309651H1
<300> PUBLICATION INFORMATION:

<400> SEQUENCE: 12
ccggaccaag gtgctggctc agttcggaga gagggcctca gaggtctgtc tggatgacac    60
agtgaccaca gagaaggagc tggacactgt ggaagtgctg aaagaattca gaaagccaag   120
gaggtcaagt ccaaactgag caacccagag aagaaggtg gtgaagactc ccggctctca    180
gctgccccct gcatcagacc cagcagctcc cctcccactg tggctcccgc atctgcctcc   240
ctgccccagc ccatcctct                                                259

<210> SEQ ID NO 13
<211> LENGTH: 239
<212> TYPE: DNA
<213> ORGANISM: Homo sapiens
<220> FEATURE:
<221> NAME/KEY:
<223> OTHER INFORMATION: 1659790H1
<300> PUBLICATION INFORMATION:

<400> SEQUENCE: 13
cccattgccc agggatgttc tgattccttg gagtccatcc ctgcgggaca ggcagcttcc    60
gatgatttaa gggacgtgcc aggagctgtt ggtggtgcaa gcccagaaca tgccgagccg   120
gaggtccagg tggtgccggg gtctggccag atcatcttcc tgcccttcac ctgcattggc   180
tacacggcca ccaatcagga cttcatccag cgcctgagca cactgatccg gcaggccat   239

<210> SEQ ID NO 14
<211> LENGTH: 236
<212> TYPE: DNA
<213> ORGANISM: Homo sapiens
<220> FEATURE:
<221> NAME/KEY:
<223> OTHER INFORMATION: 5505610H1
<300> PUBLICATION INFORMATION:

<400> SEQUENCE: 14
cctgcattgg ctacacggcc accaatcagg acttcatcca gcgcctgagc acactgatcc    60
ggcaggccat cgagcggcag ctgcctgcct ggatcgaggc tgccaaccag cgggaggagg   120
gccagggtga acaggcgag gaggaggatg aggaggagga agaagaggag acgtggctg    180 agaaccgcta ctttgaaatg gggcccccag acgtggagga ggaggaggga ggaggc      236

<210> SEQ ID NO 15
<211> LENGTH: 248
<212> TYPE: DNA
<213> ORGANISM: Homo sapiens
<220> FEATURE:
<221> NAME/KEY: unsure
<222> LOCATION: 70
<223> OTHER INFORMATION: a or g or c or t, unknown, or other
<220> FEATURE:
<221> NAME/KEY:
<223> OTHER INFORMATION: 4745071H1
<300> PUBLICATION INFORMATION:

<400> SEQUENCE: 15
gagaaccgct actttgaaat ggggccccca gacgtggagg aggaggaggg aggaggccag    60
ggggaggaan aggaggagga agaggaggat gaagaggccg aggaggagcg cctggctctg   120
```
gaatgggccc tgggcgcgga cgaggacttc ctgctggagc acatccgcat cctcaaggtg      180
cagtggtgct tcctgatcca tgtgcagggc agtatccgcc agttcgccgc ctgccttgtg      240
ctcaccga                                                               248

<210> SEQ ID NO 16
<211> LENGTH: 268
<212> TYPE: DNA
<213> ORGANISM: Homo sapiens
<220> FEATURE:
<221> NAME/KEY: unsure
<222> LOCATION: 17,18,27,179,183,234
<223> OTHER INFORMATION: a or g or c or t, unknown, or other
<220> FEATURE:
<221> NAME/KEY:
<223> OTHER INFORMATION: 4640790H1
<300> PUBLICATION INFORMATION:

<400> SEQUENCE: 16
ggatgaagag gccgagnngg agcgccnggc tctggaatgg gccctgggcg cggacgagga      60
cttcctgctg gagcacatcc gcatcctcaa ggtgctgtgg tgcttcctga tccatgtgca     120
gggcagtatc cgccagttcg ccgcctgcct tgtgctcacc gacttcggca tcgcagtcnt     180
cgngatcccg caccaggagt ctcggggcag cagccagcac atcctctcct cccngcgctt     240
tgtcttttgc ttcccgcatg gcgacctc                                        268

<210> SEQ ID NO 17
<211> LENGTH: 247
<212> TYPE: DNA
<213> ORGANISM: Homo sapiens
<220> FEATURE:
<221> NAME/KEY: unsure
<222> LOCATION: 211,214,219,227
<223> OTHER INFORMATION: a or g or c or t, unknown, or other
<220> FEATURE:
<221> NAME/KEY:
<223> OTHER INFORMATION: 3087155F6
<300> PUBLICATION INFORMATION:

<400> SEQUENCE: 17
ggagcgcctg gctctggaat gggccctggg cgcggacgag gacttcctgc tggagcacat      60
ccgcatcctc aaggtgctgt ggtgcttcct gatccatgtg cagggcagta tccgccagtt     120
cgccgcctgc cttgtgctca ccgacttcgg catcgcagtc ttcgagatcc gcaccagga     180 gtctcggggc agcagccagc acatcctctc ntcncgaang ctttgtnctt tgcttcccgc     240
atggcga                                                               247

<210> SEQ ID NO 18
<211> LENGTH: 210
<212> TYPE: DNA
<213> ORGANISM: Homo sapiens
<220> FEATURE:
<221> NAME/KEY: unsure
<222> LOCATION: 125
<223> OTHER INFORMATION: a or g or c or t, unknown, or other
<220> FEATURE:
<221> NAME/KEY:
<223> OTHER INFORMATION: 4834547H1
<300> PUBLICATION INFORMATION:

<400> SEQUENCE: 18
tcttcgagat cccgcaccag gagtctcggg gcagcagcca gcacatcctc ctcctccctg      60
cgctttgtct tttgcttccc gcatggcgac ctcaccgagt ttggcttcct catgccggag     120

```
ctgtnctctgg tgctcaaggt acggcacagt gagaacacgc tcttcattat ctcggacgcc        180
gccaacctgc acgagttcca cacaacatac                                          210
```

<210> SEQ ID NO 19
<211> LENGTH: 320
<212> TYPE: DNA
<213> ORGANISM: Homo sapiens
<220> FEATURE:
<221> NAME/KEY: unsure
<222> LOCATION: 252
<223> OTHER INFORMATION: a or g or c or t, unknown, or other
<220> FEATURE:
<221> NAME/KEY:
<223> OTHER INFORMATION: 2482087H1
<300> PUBLICATION INFORMATION:

<400> SEQUENCE: 19

```
caccgagttt ggcttcctca tgccggagct gtgtctggtg ctcaaggtac ggcacagtga         60
gaacacgctc ttcattatct cggacgccgc caacctgcac gagttccacg cggacctgcg        120
ctcatgcttt gcaccccagc acatggccat gctgtgtagc cccatcctct acggcagcca       180
caccagcctg caggagttcc tgcgccagct gctcaccttc tacaaggtgg ctggcggctg       240
ccaggagcgc ancagggctg cttccccgtc tacctggtct acagtgacaa gcgcatggtg       300
cagacggccg ccggggatta                                                    320
```

<210> SEQ ID NO 20
<211> LENGTH: 288
<212> TYPE: DNA
<213> ORGANISM: Homo sapiens
<220> FEATURE:
<221> NAME/KEY: unsure
<222> LOCATION:
<221> NAME/KEY: unsure
<222> LOCATION: 204,227,243,260
<223> OTHER INFORMATION: a or g or c or t, unknown, or other
<220> FEATURE:
<221> NAME/KEY:
<223> OTHER INFORMATION: 396596H1
<300> PUBLICATION INFORMATION:

<400> SEQUENCE: 20

```
gnctgcagga gttctgcggc agtgntcanc ttctacaagg tggntngcgg ntnccaggag         60
cgcagcaggg ntncttttccc gtctanctgg nntacagtna caagcgnatg gtgcagacgg      120
ccggcgggga ctactnaggc aaaatcgagt gggncagctn caaaatntgt tcagccgtgc      180
ggcggttctg ntncggggcc tntnaggccg tcaagttcgc cggcatnccc tacttggttt      240 ttntttaaggc ccagcaactn aaagtcaatc aagggcgatt taaaccca                  288
```

<210> SEQ ID NO 21
<211> LENGTH: 455
<212> TYPE: DNA
<213> ORGANISM: Homo sapiens
<220> FEATURE:
<221> NAME/KEY:
<223> OTHER INFORMATION: 2300531R6
<300> PUBLICATION INFORMATION:

<400> SEQUENCE: 21

```
ggcaacatcg agtgggccag ctgcacactc tgttcagccg tgcggcgctc ctgctgcgcg         60
ccctctgagg ccgtcaagtc cgccgccatc ccctactggc tgttgctcac gcccagcac       120 ctcaacgtca tcaaggccga cttcaacccc atgcccaacc gtggcaccca caactgtcgc      180
aaccgcaaca gcttcaagct cagccgtgtg ccgctctcca ccgtgctgct ggaccccaca      240
```

```
cgcagctgta cccagcctcg gggcgccttt gctgatggcc acgtgctaga gctgctcgtg    300
gggtaccgct tgtcactgc catcttcgtg ctgccccacg agaagttcca cttcctgcgc     360
gtctacaacc agctgcgggc ctcgctgcag gacctgaaga ctgtggtcaa tcgccaagac    420
ccccgggacg gaaggcagcc cccagggctc ctttg                               455
```

<210> SEQ ID NO 22
<211> LENGTH: 541
<212> TYPE: DNA
<213> ORGANISM: Homo sapiens
<220> FEATURE:
<221> NAME/KEY: unsure
<222> LOCATION:
<221> NAME/KEY: unsure
<222> LOCATION: 502,508,509,516,519,523,530,531,538
<223> OTHER INFORMATION: a or g or c or t, unknown, or other
<220> FEATURE:
<221> NAME/KEY:
<223> OTHER INFORMATION: 2858139F6
<300> PUBLICATION INFORMATION:

<400> SEQUENCE: 22

```
cctcaacgtc atcaaggccg acttcaaccc catgcccaac cgtggcaccc acaactgtcg    60
caaccgcaac agcttcaagc tcagccgtgt gccgctctcc accgtgctgc tggaccccac   120
acgcagctgt acccagcctc ggggcgcctt tgctgatggc cacgtgctag agctgctcgt   180
ggggtaccgc tttgtcactg ccatcttcgt gctgccccac gagaagttcc acttcctgcg   240
cgtctacaac cagctgcggg cctcgctgca ggacctgaag actgtggtca tcgccaagac   300
ccccgggacg ggangcagnc ccagngntc ctttgcggat ggccagcctg ccgagcgcag   360
ggccagcaat gaccagcgtc cccaggaagg tcccagcaga ngctctggcc ccgggcccca   420
atggaangtc ccangctncc aggncccttg caagnagcct tcaggccntc aaggggngaa   480
ngcngaagan ttnntgngcc cnaagganna agggcnttna aantttaaan nttttggntc   540
c                                                                     541
```

<210> SEQ ID NO 23
<211> LENGTH: 526
<212> TYPE: DNA
<213> ORGANISM: Homo sapiens
<220> FEATURE:
<221> NAME/KEY: unsure
<222> LOCATION: 376,413
<223> OTHER INFORMATION: a or g or c or t, unknown, or other
<220> FEATURE:
<221> NAME/KEY:
<223> OTHER INFORMATION: 2096273R6
<300> PUBLICATION INFORMATION:

<400> SEQUENCE: 23

```
agaagttcca cttcctgcgc gtctacaacc agctgcgggc ctcgctgcag gacctgaaga    60
ctgtggtcat cgccaagacc cccgggacgg gaggcagccc ccagggctcc tttgcggatg   120
gccagcctgc cgagcgcagg gccagcaatg accagcgtcc ccaggaggtc ccagcagagg   180
ctctggcccc ggccccagtg gaagtccag ctccagcccc tgcagcagcc tcagcctcag    240
gcccagcgaa gactccggcc ccagcagagg cctcaacttc agctttggtc ccagaggaga   300
cgccagtgga agctccagcc caccccag ccgaggcccc tgcccagtac ccgagtgagc     360
acctcatcca ggccanctcg gaggagaatc agattccctc gcacttgcct gcntgcacgt   420
cgctccggca cgtcgccagc ctgcggggca gcggcatcat cgagctcttc cacagcagca   480
```

```
ttgctgaggt tgaaaacgag ggagctgagg gaactcatgt ggttct              526
```

<210> SEQ ID NO 24
<211> LENGTH: 247
<212> TYPE: DNA
<213> ORGANISM: Homo sapiens
<220> FEATURE:
<221> NAME/KEY:
<223> OTHER INFORMATION: 2521806H1
<300> PUBLICATION INFORMATION:

<400> SEQUENCE: 24

```
cagatcccct cgcacttgcc tgcctgcccg tcgctccggc acgtcgccag cctgcggggc    60
agcgccatca tcgagctctt ccacagcagc attgctgagg ttgaaaacga ggagctgagg   120
cacctcatgt ggtcctcggt ggtgttctac cagacccag ggctggaggt gactgcctgc   180
gtgctgctct ccaccaaggc tgtgtacttt gtgctccacg acggcctccg ccgctacttc   240
tcagagc                                                            247
```

<210> SEQ ID NO 25
<211> LENGTH: 590
<212> TYPE: DNA
<213> ORGANISM: Homo sapiens
<220> FEATURE:
<221> NAME/KEY: unsure
<222> LOCATION: 461,517,526,535,536,561
<223> OTHER INFORMATION: a or g or c or t, unknown, or other
<220> FEATURE:
<221> NAME/KEY:
<223> OTHER INFORMATION: 1886951F6
<300> PUBLICATION INFORMATION:

<400> SEQUENCE: 25

```
gttctaccag accccagggc tggaggtgac tgcctgcgtg ctgctctcca ccaaggctgt    60
gtactttgtg ctccacgacg gcctccgccg ctacttctca gagccactgc aggatttctg   120
gcatcagaaa aacaccgact acaacaacag ccctttccac atctcccagt gcttcgtgct   180
aaagcttagt gacctgcagt cagtcaatgt ggggcttttc gaccagcatt tccggctgac   240
gggttccacc ccgatgcagg tggtcacgtg cttgacgcgg acagctacc tgacgcactg   300 cttcctccag cacctcatgg tcgtgctgtc ctctctggaa cgcacgccct cgccggagcc   360
tgttgacaag gattctactc cgagtttggg aacaagacca cagggaagat ggagaactac   420
gagctgatcc actctagtcg cgtcaagttt acctacccca ntggaggaag gagattgggg   480
gacctgaacg tttcactgtg gcccaaaaag attggcngaa gccagnagaa agggnnccag   540
cccttcaagc atcctggctg ntacgtgcaa ggctttccaa ggtggggatg              590
```

<210> SEQ ID NO 26
<211> LENGTH: 266
<212> TYPE: DNA
<213> ORGANISM: Homo sapiens
<220> FEATURE:
<221> NAME/KEY:
<223> OTHER INFORMATION: 2204546H1
<300> PUBLICATION INFORMATION:

<400> SEQUENCE: 26

```
gctgtcctct ctggaacgca cgccctcgcc ggagcctgtt gacaaggact tctactccga    60
gtttgggaac aagaccacag ggaagatgga gaactacgag ctgatccact ctagtcgcgt   120
caagtttacc taccccagtg aggaggagat tggggacctg acgttcactg tggcccaaaa   180
gatggctgag ccagagaagg ccccagccct cagcatcctg ctgtacgtgc aggccttcca   240
```
ggtgggcatg ccaccccctg ggtgct                                                266

<210> SEQ ID NO 27
<211> LENGTH: 579
<212> TYPE: DNA
<213> ORGANISM: Homo sapiens
<220> FEATURE:
<221> NAME/KEY: unsure
<222> LOCATION: 439,508,540,549,562,575
<223> OTHER INFORMATION: a or g or c or t, unknown, or other
<220> FEATURE:
<221> NAME/KEY:
<223> OTHER INFORMATION: 1540117R1
<300> PUBLICATION INFORMATION:

<400> SEQUENCE: 27
aggccccagc cctcagcatc ctgctgtacg tgcaggcctt ccaggtgggc atgccacccc    60
ctgggtgctg caggggcccc ctgcgcccca agacactcct gctcaccagc tccgagatct  120
tcctcctgga tgaggactgt gtccactacc cactgcccga gtttgccaaa gagccgccgc  180
agagagacag gtaccggctg gacgatggcc gccgcgtccg ggacctggac cgagtgctca  240
tgggctacca gacctacccg caggccctca ccctcgtctt cgatgacgtg caaggtcatg  300
acctcatggg cagtgtcacc ctggaccact ttggggaggt gccaggtggc ccggctagag  360
ccagccaggg ccgtgaagtc cagtggcagg tgtttgtccc cagtgctgag agcagagaga  420
agctcatctc gctgttggnt cgccagtggg aggccctgtg tggccgtgag ctgcctgtcg  480
agctcaacgg ctagcccagg ccacagcnag ctgtcgtgtc cagctgacgc ctaattgggn  540
agggaagang gttttgtgtt cncaaaaatg tttanccccc                         579

<210> SEQ ID NO 28
<211> LENGTH: 621
<212> TYPE: DNA
<213> ORGANISM: Homo sapiens
<220> FEATURE:
<221> NAME/KEY: unsure
<222> LOCATION: 11,536
<223> OTHER INFORMATION: a or g or c or t, unknown, or other
<220> FEATURE:
<221> NAME/KEY:
<223> OTHER INFORMATION: 1724089F6
<300> PUBLICATION INFORMATION:

<400> SEQUENCE: 28
ggaccacttt ngggaggtgc caggcggccc ggctagagcc agccagggcc gtgaagtcca    60
gtggcaggtg tttgtcccca gtgctgagag cagagagaag ctcatctcgc tgttggctcg  120
ccagtgggag gccctgtgtg gccgtgagtg cctgtcgagc tcaccggcta gcccaggcca  180
cagccagcct gtcgtgtcca gcctgacgcc tactggggca gggcagcagg cttttgtgtt  240
ctctaaaaat gttttatcct ccctttggta ccttaatttg actgtcctcg cagagaatgt  300
gaacatgtgt gtgtgttgtg ttaattcttt ctcatgttgg gagtgagaat gccgggcccc  360
tcagggctgt cggtgtgctg tcagctcccc acaggtggta cagccgtgca ccagtgtc    420
gtgtctgctg ttgtgggacc gttgttaaca cgtgacatgt gggtctgatt tctctctaca  480
cgtcctttcc tgaagtgtcg agtccaagtc cttttgttgt gttgctgttg ctggtngtgt  540
tgctgttggg catcttgctg gtaatcctga aggttggtaa gcaaaaatgc acatttggaa  600
gtcccaaccc aatattgttt t                                             621

<210> SEQ ID NO 29

<211> LENGTH: 503
<212> TYPE: DNA
<213> ORGANISM: Homo sapiens
<220> FEATURE:
<221> NAME/KEY: unsure
<222> LOCATION:
<221> NAME/KEY: unsure
<222> LOCATION:
<221> NAME/KEY: unsure
<222> LOCATION: 491,492
<223> OTHER INFORMATION: a or g or c or t, unknown, or other
<220> FEATURE:
<221> NAME/KEY:
<223> OTHER INFORMATION: 1809315F6
<300> PUBLICATION INFORMATION:

<400> SEQUENCE: 29

```
tgtgtgtgtt gtgttaattc tttctcatgt tgggagtgag aatgccgggn ccctcagggc      60
tgtcggtgtg ctgtcagcct cccacaggtg gtacagccgt gcacaccagt gtcgtgtctg     120
ctgttgtggg accgttgtta acacgtgaca ctgtgggtct gactttctct tctacacgtc     180
ctttcctgaa gtgtcgagtc cagtcctttg ttgctgttgc tgttgctgtt gctgttgctg     240
ttggcatctt gctgctaatc ctgaggctgg tagcagaatg cacattggaa gctctcaccc     300
catattgttc ttcaaagtgg aggtctcccc tgatccagac aagtgggaga gcccgtgggg     360
gcagggact ggagctgcca gcaacaagcg tgaatcctgt gcctgtatct ctaatccaat      420
aaagcagagt tgacaccgg aaaaaaaaaa aannnnnann nnnnnnnnnn annnnnnnng      480
nnnnnnnnnn nnaaaaaaaa aag                                              503
```

<210> SEQ ID NO 30
<211> LENGTH: 226
<212> TYPE: DNA
<213> ORGANISM: Macaca fascicularis
<220> FEATURE:
<221> NAME/KEY:
<223> OTHER INFORMATION: 700708590H1
<300> PUBLICATION INFORMATION:

<400> SEQUENCE: 30

```
ctggatctcc gggacaacag gattgaacag atggaggagg tccggagcat aggtagcctc      60
ccgtgtctgg agcacgtgtc tctgctgaac aaccctctga gcatcatccc cgactaccgg     120
accaaggtgc tggctcagtt cggagagagg gcctcagagg tctgtctgga tgacacagtg     180
accacagaga aggagctgga cactgtggaa gtgctgaaag caattc                    226
```

<210> SEQ ID NO 31
<211> LENGTH: 244
<212> TYPE: DNA
<213> ORGANISM: Macaca fascicularis
<220> FEATURE:
<221> NAME/KEY:
<223> OTHER INFORMATION: 700720751H1
<300> PUBLICATION INFORMATION:

<400> SEQUENCE: 31

```
cccagctcca gccctggca gcagcctcag cctcaggccc agggaagact ccggccccag       60
cagagacctc aacttcaact ttggtcccag aggagacccc agtggaggct ccagccccac     120
ccccagccga agccctgcc cagtacccga gcgagcacct catccaggcc acctcggagg      180
agaatcagat cccctcgcac ttgcctgcct gcccatcact ccggcacgtc gccagcctgc     240
gggg                                                                   244
```

```
<210> SEQ ID NO 32
<211> LENGTH: 243
<212> TYPE: DNA
<213> ORGANISM: Macaca fascicularis
<220> FEATURE:
<221> NAME/KEY: unsure
<222> LOCATION: 11,30,40,44,52,66,75,82,85,129,137,157,191,194,199,201,
<222> LOCATION: 211,214,219,231
<221> NAME/KEY: unsure
<222> LOCATION: 242
<223> OTHER INFORMATION: a or g or c or t, unknown, or other
<220> FEATURE:
<221> NAME/KEY:
<223> OTHER INFORMATION: 700705986H1
<300> PUBLICATION INFORMATION:

<400> SEQUENCE: 32
gccacctcgg nggagaatca gatcccctcn cacttgcctn cctncccatc antccggcac      60
gtacgntagc ctgcngggca gngcnatcat cgagctctcc acagcagcat tgctgagggt     120
gaaaacgang agctgangca cctcatgtgg tcctcgntgg tgttctacca gaccccaggg     180
cttgaggtga ncgnctgcnt nctgctctct nacnaaggnt gtgtactttg ngctccatga     240 cng                                                                  243

<210> SEQ ID NO 33
<211> LENGTH: 275
<212> TYPE: DNA
<213> ORGANISM: Mus musculus
<220> FEATURE:
<221> NAME/KEY:
<223> OTHER INFORMATION: 701251065H1
<300> PUBLICATION INFORMATION:

<400> SEQUENCE: 33
cgtctctcag tgctttgtgt tgaaactcag tgacctgcag tcagtcaacg tcggcctttt      60
cgaccagtac ttccggctga cgggctcctc cccgacgcag tggtcacgt gcttgactcg      120 cgacagctac ctgacgcact gcttcctcca gcatctgatg cttgtgctgt cctccctgga     180
gcgcacaccc tcgcctgagc ctgttgacaa ggacttctac tcagaattgg ggacaagaat     240
acagggaaaa tggagaacta tgagctgatc catcc                                275

<210> SEQ ID NO 34
<211> LENGTH: 249
<212> TYPE: DNA
<213> ORGANISM: Mus musculus
<220> FEATURE:
<221> NAME/KEY:
<223> OTHER INFORMATION: 701087190H1
<300> PUBLICATION INFORMATION:

<400> SEQUENCE: 34
aagaatacag ggaaaatgga gaactatgag ctgatccatt ccagccgcgt caagttcacc      60
taccccagtg aggaagaggt tggggacctg acctatattg tcgcacagaa gatggctgat     120
cctgcaaaga atccagccct cagcatctta ctgtacatcc aggccttcca ggtggtcaca     180
ccacaccttg gcgggggcag gggcccactg cgccctaaga cgctgctcct gaccagcgcc     240
gagatcttc                                                            249

<210> SEQ ID NO 35
<211> LENGTH: 221
<212> TYPE: DNA
<213> ORGANISM: Rattus norvegicus
<220> FEATURE:
<221> NAME/KEY: unsure
```

```
<222> LOCATION: 56,209,211,215
<223> OTHER INFORMATION: a or g or c or t, unknown, or other
<220> FEATURE:
<221> NAME/KEY:
<223> OTHER INFORMATION: 700329107H1
<300> PUBLICATION INFORMATION:

<400> SEQUENCE: 35
ggcacagaag gacctttttgg gaccagcaat attcgagagc agctcctgcc ctttgntctt    60
tcgatattca agtctcttca ccaggtggag atgagttcac tgtgatgcca agcatgtacc   120
gagggctggt cacctccaag ccaacactgg ccacaatgag cgttagattc tcagcagcct   180
caatgaagga agttcttgtt ccagaagcng naganttttgc t                      221

<210> SEQ ID NO 36
<211> LENGTH: 309
<212> TYPE: DNA
<213> ORGANISM: Rattus norvegicus
<220> FEATURE:
<221> NAME/KEY:
<223> OTHER INFORMATION: 700292102H1
<300> PUBLICATION INFORMATION:

<400> SEQUENCE: 36
gcacaaactc tattccctgg ttaatctgga cctcagagac aaccggattg agcagttgga    60
tgaagtcaag agcataggca acctgccgtg tctggagcac gtggccctgc taaacaaccc   120
tctgagcatc atccctgact accggaccaa ggtgctttcc cagtttggag aacgagcctc   180
tgagatctgt ctagatgatg tcgcaaccac agagaaggaa tggacactgt ggaagtgcta   240
aaggccattc agaaagccaa agacgtcagt ccaaatgagc agcacagaaa agaagttggt   300
gaggattcc                                                           309

<210> SEQ ID NO 37
<211> LENGTH: 307
<212> TYPE: DNA
<213> ORGANISM: Rattus norvegicus
<220> FEATURE:
<221> NAME/KEY: unsure
<222> LOCATION: 92,212,253,278,289,293
<223> OTHER INFORMATION: a or g or c or t, unknown, or other
<220> FEATURE:
<221> NAME/KEY:
<223> OTHER INFORMATION: 700278887H1
<300> PUBLICATION INFORMATION:

<400> SEQUENCE: 37
cagcctgcaa gagttcttgc gccagctggc tcaccttcta caaggtggcc ggtggctctc    60
aggagcgcaa ccagggctgc ttccctgtct anctggtgta cagcgacaag cgcatggtgc   120
agacggctgc cggggactac tcaggcaaca tcgagtgggc cagctgcacg ctgtgctccg   180
cagtgcggcg ttcctgctgc gcaccctctg angccgtcaa gtctgccgcc atcccctact   240
ggctgctgct cantcccagc attcaacgtc atcaaagncg acttcaacnc atgnccagtc   300
gtggcac                                                             307

<210> SEQ ID NO 38
<211> LENGTH: 296
<212> TYPE: DNA
<213> ORGANISM: Rattus norvegicus
<220> FEATURE:
<221> NAME/KEY: unsure
<222> LOCATION: 84
<223> OTHER INFORMATION: a or g or c or t, unknown, or other
<220> FEATURE:
```

```
<221> NAME/KEY:
<223> OTHER INFORMATION: 700057363H1
<300> PUBLICATION INFORMATION:

<400> SEQUENCE: 38
aaggccgact tcaaccccat gcccagtcgt ggcacccaca actgtcgcaa ccgcaacagc      60
ttcaagctta gccgcgtccc gctnctccac cgtgctgctg gacccactc gcagctgcac     120 ccagccacgg ggagccttcg ccgatggcca tgtgctcgag ctgcttgttg gctaccgctt    180
tgttaccgcc atctttgtgc tgccccacga gaaattccac ttcctgcgag tctacaatca    240
gctccgcgcc tcactgaagg acctgaagac tgtggtcatc gccaagaatc cttccg        296

<210> SEQ ID NO 39
<211> LENGTH: 123
<212> TYPE: DNA
<213> ORGANISM: Rattus norvegicus
<220> FEATURE:
<221> NAME/KEY: unsure
<222> LOCATION: 71
<223> OTHER INFORMATION: a or g or c or t, unknown, or other
<220> FEATURE:
<221> NAME/KEY:
<223> OTHER INFORMATION: 700810051H1
<300> PUBLICATION INFORMATION:

<400> SEQUENCE: 39
ctccagtgga ggcccaagca gaggtccctg ctcagtatcc aagtgagcgc ctaatccagt      60
ccacgtctga ngagaatcag atccttcta cacttgccag tctgcccatc actccagcac     120
atc                                                                  123

<210> SEQ ID NO 40
<211> LENGTH: 283
<212> TYPE: DNA
<213> ORGANISM: Rattus norvegicus
<220> FEATURE:
<221> NAME/KEY: unsure
<222> LOCATION: 208,256,266,271,273,281
<223> OTHER INFORMATION: a or g or c or t, unknown, or other
<220> FEATURE:
<221> NAME/KEY:
<223> OTHER INFORMATION: 700068150H1
<300> PUBLICATION INFORMATION:

<400> SEQUENCE: 40
cgcccgtctt cggggcgcg ccatcattga cctcttccac agcagcattg ccgaggttga      60
aaacgaggag ctaaggcacc tcctgtggtc gtcagtggtg ttctaccaga ccccgggct     120 ggaagtgacc gcctgtgtgc tgctgtccac caaggctgtg tacttcatac tgatgatggc    180
tccgccggta cttctctgaa ccgtgcanga ttctggaaca gaaaacatga ctataacaca    240
gtctttcaca ttctantgct tgtgcncaac nantgactga ngc                      283

<210> SEQ ID NO 41
<211> LENGTH: 251
<212> TYPE: DNA
<213> ORGANISM: Rattus norvegicus
<220> FEATURE:
<221> NAME/KEY: unsure
<222> LOCATION: 37,131,133,135,245
<223> OTHER INFORMATION: a or g or c or t, unknown, or other
<220> FEATURE:
<221> NAME/KEY:
<223> OTHER INFORMATION: 701024483H1
<300> PUBLICATION INFORMATION:

<400> SEQUENCE: 41
```

```
gctgtccacc aaggctgtgt acttcatact gcatganggc ctccgccggt acttctctga    60
accgctgcag gatttctggc accagaaaaa cactgactat aacaacagtc ctttccacat   120
ctctcagtgc ncntntgctc aaactcagtg acctgcagtc agtcaacgtc ggccttttcg   180
atcaggactt ccggctgacg ggctcttccc cgacgcaggt ggtcacatgc ttgactcgag   240
acagntacct g                                                        251
```

<210> SEQ ID NO 42
<211> LENGTH: 255
<212> TYPE: DNA
<213> ORGANISM: Rattus norvegicus
<220> FEATURE:
<221> NAME/KEY: unsure
<222> LOCATION: 31
<223> OTHER INFORMATION: a or g or c or t, unknown, or other
<220> FEATURE:
<221> NAME/KEY:
<223> OTHER INFORMATION: 701289331H1
<300> PUBLICATION INFORMATION:

<400> SEQUENCE: 42

```
ggctgacggg ctcttccccg acgcaggtgg ncacatgctt gactcgagac agctacctga    60
cacactgctt cctgcagcac cttatgctag tgctgtcctc cctggagcgc acaccttcac   120
ccgagcctat tgacaaggac ttctactcag aatttgggga caagaataca gggaaaatgg   180
agaactatga gctgatccat tccagccgcg caagttcacc tacccagtg aggaagaggc   240 cggggacctg accta                                                    255
```

<210> SEQ ID NO 43
<211> LENGTH: 181
<212> TYPE: DNA
<213> ORGANISM: Rattus norvegicus
<220> FEATURE:
<221> NAME/KEY:
<223> OTHER INFORMATION: 700230141H1
<300> PUBLICATION INFORMATION:

<400> SEQUENCE: 43

```
agctgatcca ttccagccgc gtcaagttca cctaccccag tgaggaagag gtcggggacc    60
tgacctatgt tgtggcacag aagatggctg accctgccaa gaatccagcc ctcagcatct   120
tattgtacat ccaggccttc caggtgatca caccccagct tgggcggggc aggggcccat   180
a                                                                   181
```

<210> SEQ ID NO 44
<211> LENGTH: 245
<212> TYPE: DNA
<213> ORGANISM: Rattus norvegicus
<220> FEATURE:
<221> NAME/KEY:
<223> OTHER INFORMATION: 701273187H1
<300> PUBLICATION INFORMATION:

<400> SEQUENCE: 44

```
atccattcca gccgcgtcaa gttcacctac cccagtgagg aagaggtcgg ggacctgacc    60
tatcttgtgg cacagaagat ggctgaccct gccaagaatc cagccctcag catcttattg   120
tacatccagg ccttccaggt gatcacaccc cagcttgggc ggggcagggg cccactacgc   180
cctaagacac tcctactgac cagtgctgag atctttctcc tggacgagga ctacatccac   240
tatcc                                                               245
```

<210> SEQ ID NO 45
<211> LENGTH: 343
<212> TYPE: DNA
<213> ORGANISM: Rattus norvegicus
<220> FEATURE:
<221> NAME/KEY: unsure
<222> LOCATION: 85,88,96,329
<223> OTHER INFORMATION: a or g or c or t, unknown, or other
<220> FEATURE:
<221> NAME/KEY:
<223> OTHER INFORMATION: 700514583H1
<300> PUBLICATION INFORMATION:

<400> SEQUENCE: 45

| | | | | | |
|---|---|---|---|---|---|
| cacaccccag | cttgggcggg | gcaggggccc | actacgccct | aagacactcc | tactgaccag | 60 |
| tgctgagatc | tttctcctgg | acganggnct | acatcnacta | tccattgcct | gaatttgcca | 120 |
| aagagccacc | acagagggac | agataccggc | tagacgatgg | ccgccgtgtc | cgggatttag | 180 |
| accgggtgct | catgggctca | atccctaccc | acaggccctc | actcttgttt | ttgatgacac | 240 |
| gcagggccac | gacctcatgg | ggagtgtcac | cctggaccat | cgggagat | ccgggtggc | 300 |
| ctggtagggt | gggcagggcg | ggagtgcant | ggcagtgttt | gtc | | 343 |

<210> SEQ ID NO 46
<211> LENGTH: 248
<212> TYPE: DNA
<213> ORGANISM: Rattus norvegicus
<220> FEATURE:
<221> NAME/KEY:
<223> OTHER INFORMATION: 700768834H1
<300> PUBLICATION INFORMATION:

<400> SEQUENCE: 46

| | | | | | |
|---|---|---|---|---|---|
| tgtttttgat | gacacgcagg | gccacgacct | catggggagt | gtcaccctgg | accacttcgg | 60 |
| ggagatgccg | gtggccctg | gtagggctgg | gcagggccgg | gaggtgcagt | ggcaggtgtt | 120 |
| tgtgcccagt | gcgagagccg | agaaaagctg | atctcactgc | tcgcacggca | gtgggaagct | 180 |
| ctctgtggca | gggagctgcc | tgtggagctc | actggctagt | gcgcgggcag | cccggcctcc | 240 |
| tgccgtgc | | | | | | 248 |

<210> SEQ ID NO 47
<211> LENGTH: 559
<212> TYPE: PRT
<213> ORGANISM: Homo sapiens
<220> FEATURE:
<221> NAME/KEY:
<223> OTHER INFORMATION: W43396
<300> PUBLICATION INFORMATION:

<400> SEQUENCE: 47

Met Thr Gly Gln Val Gly Ala Gln Thr Val Ser Gly Gly Lys Arg
 1               5                  10                  15

Ser Ile Ala Gly Leu Thr Leu Val Arg Pro Leu Arg Ser Val His
                20                  25                  30

Leu Leu Asp Met Ser Val Gln Val Ile Arg Pro Gly Glu Ala Phe
                35                  40                  45

Pro Thr Ala Leu Ala Asp Val Arg Trp Asn Ser Pro Glu Lys Lys
                50                  55                  60

Gly Gly Glu Asp Ser Arg Leu Ser Ala Ala Pro Cys Ile Arg Pro
            65                  70                  75

Ser Ser Ser Pro Pro Thr Val Ala Pro Ala Ser Ala Ser Leu Pro
                80                  85                  90

-continued

```
Gln Pro Ile Leu Ser Asn Gln Gly Ile Met Phe Val Gln Glu Glu
                 95                 100                 105
Ala Leu Ala Ser Ser Leu Ser Ser Thr Asp Ser Leu Thr Pro Glu
            110                 115                 120
His Gln Pro Ile Ala Gln Gly Cys Ser Asp Ser Leu Glu Ser Ile
            125                 130                 135
Pro Ala Gly Gln Ala Ala Ser Asp Asp Leu Arg Asp Val Pro Gly
            140                 145                 150
Ala Val Gly Gly Ala Ser Pro Glu His Ala Glu Pro Glu Val Gln
            155                 160                 165
Val Val Pro Gly Ser Gly Gln Ile Ile Phe Leu Pro Phe Thr Cys
            170                 175                 180
Ile Gly Tyr Thr Ala Thr Asn Gln Asp Phe Ile Gln Arg Leu Ser
            185                 190                 195
Thr Leu Ile Trp Gln Ala Ile Glu Trp Gln Leu Pro Ala Trp Ile
            200                 205                 210
Glu Ala Ala Asn Gln Trp Glu Glu Gly Gln Gly Glu Gln Gly Glu
            215                 220                 225
Glu Glu Asp Glu Glu Glu Glu Glu Glu Asp Val Ala Glu Asn
            230                 235                 240
Arg Tyr Phe Glu Met Gly Pro Pro Asp Val Glu Glu Glu Gly
            245                 250                 255
Gly Gly Gln Gly Glu Glu Glu Glu Glu Glu Asp Glu Glu
            260                 265                 270
Ala Glu Glu Glu Arg Leu Ala Leu Glu Trp Ala Leu Gly Ala Asp
            275                 280                 285
Glu Asp Phe Leu Leu Glu His Ile Arg Ile Leu Lys Val Leu Trp
            290                 295                 300
Cys Phe Leu Ile His Val Gln Gly Ser Ile Arg Gln Phe Ala Ala
            305                 310                 315
Cys Leu Val Leu Thr Asp Phe Gly Ile Ala Val Phe Glu Ile Pro
            320                 325                 330
His Gln Glu Ser Trp Gly Ser Ser Gln His Ile Leu Ser Ser Leu
            335                 340                 345
Arg Phe Val Phe Cys Phe Arg Met Ala Thr Ser Pro Ser Leu Ala
            350                 355                 360
Ser Ser Cys Trp Ser Cys Val Trp Cys Ser Arg Tyr Gly Thr Val
            365                 370                 375
Arg Thr Arg Ser Ser Leu Ser Trp Thr Pro Pro Thr Cys Thr Ser
            380                 385                 390
Ser Thr Trp Thr Cys Ala His Ala Leu His Pro Ser Thr Trp Pro
            395                 400                 405
Cys Cys Val Ala Pro Ser Ser Thr Ala Thr Pro Ala Cys Arg
            410                 415                 420
Ser Ser Cys Ala Ser Cys Ser Pro Ser Thr Arg Trp Leu Ala Ala
            425                 430                 435
Ala Arg Ser Ala Ala Arg Ala Ala Ser Pro Ser Thr Trp Ser Thr
            440                 445                 450
Val Thr Ser Ala Trp Cys Arg Trp Pro Pro Gly Thr Thr Gln Ala
            455                 460                 465
Thr Ser Ser Gly Pro Ala Ala His Ser Val Gln Pro Cys Gly Ala
            470                 475                 480
```

-continued

```
Pro Ala Ala Arg Pro Leu Arg Pro Ser Ser Pro Pro Pro Ser Pro
                485                 490                 495

Thr Gly Cys Cys Ser Arg Pro Ser Thr Ser Thr Ser Ser Arg Pro
                500                 505                 510

Thr Ser Thr Pro Cys Pro Thr Val Ala Pro Thr Thr Val Ala Thr
                515                 520                 525

Ala Thr Ala Ser Ser Ser Ala Val Cys Arg Ser Pro Pro Cys Cys
                530                 535                 540

Trp Thr Pro His Ala Ala Val Pro Ser Leu Gly Ala Pro Leu Leu
                545                 550                 555

Met Ala Thr Cys
```

MAMMALIAN IMIDAZOLINE RECEPTOR

FIELD OF THE INVENTION

This invention relates to nucleic acid molecules and amino acid sequences of a new mammalian protein and to their use in the characterization, diagnosis, prevention, and treatment of conditions such as hypertension, cancer, immune, and reproductive disorders.

BACKGROUND OF THE INVENTION

Phylogenetic relationships among organisms have been demonstrated many times, and studies from a diversity of prokaryotic and eukaryotic organisms suggest a more or less gradual evolution of biochemical and physiological mechanisms and metabolic pathways. Despite different evolutionary pressures, proteins that regulate the cell cycle in yeast, nematode, fly, rat, and man have common chemical and structural features and modulate the same general activity. Comparisons of human gene sequences with those from other organisms where structure and/or function are known allow researchers to draw analogies and to develop model systems for testing diagnostic and therapeutic agents for human conditions, diseases, and disorders.

Hypertension is a major cause of morbidity and mortality. It is probably the most important public health problem in developed countries, but the etiology is still largely unknown. As a result, treatment for hypertension may be nonspecific and lead to a large number of side effects and up to a 50 percent noncompliance rate. The prevalence of hypertension in the general population may vary by ethnicity, socioeconomic status, and gender. Dietary intake and genetic factors are also associated with the incidence rate of hypertension.

Hypertension is a common cause of chronic heart failure, particularly in older people whose heart muscle is weakened by age and progressive coronary valvular sclerosis. Fluid is retained by the kidneys to increase blood volume in compensation for the diminished pumping ability of the heart. Patients who develop malignant hypertension usually develop both heart and kidney failure.

Treatment of hypertension includes reduced sodium intake, weight loss, changes in living conditions, and treatment with drugs such as angiotensin II receptor antagonists, angiotensin converting enzyme inhibitors, diuretics, vasodilators, calcium channel antagonists, and antiadrenergic agents. Antiadrenergic agents may be classified into at least two groups, those which act upon the peripheral nervous system and those which act upon the central nervous system. The central acting agents are thought to act upon both adrenoreceptors and non-adrenoreceptors. Drugs such as clonidine bind to both the $a_2$ adrenoreceptor and to a non-adrenoreceptor, the imidazoline receptor. The endogenous ligands for imidazoline receptors have been identified as agmatine, a decarboxylated form of the amino acid arginine (Herman, Z. S. (1997) Pol. J. Pharmacol. 49:85–88).

The discovery of mammalian nucleic acid molecules encoding an imidazoline receptor provides new compositions which are useful in the characterization, diagnosis, prevention, and treatment of hypertension, cancer, immune, and reproductive disorders.

SUMMARY OF THE INVENTION

The invention is based on the discovery of a substantially purified mammalian nucleic acid molecules encoding a mammalian imidazoline receptor (mIR), which satisfies a need in the art by providing compositions useful in the characterization, diagnosis, prevention, and treatment of conditions such as hypertension, cancer, immune, and reproductive disorders.

The invention provides isolated and purified mammalian nucleic acid molecules comprising the nucleotides 1 to 1424 and 2311 to 5128 of SEQ ID NO:1 or fragments thereof (SEQ ID NOs:3–12 and 18–29). The invention further provides fragments homologous to the mammalian nucleic acid molecule, SEQ ID NOs:30–46, in the Sequence Listing.

The invention further provides a probe which hybridizes under high stringency conditions to the mammalian nucleic acid molecule or fragments thereof. The invention also provides isolated and purified nucleic acid molecules which are complementary to the mammalian nucleic acid molecule comprising the nucleotides 1 to 1424 and2311 to 5128 of SEQ ID NO:1 or a fragment thereof (SEQ ID NOs:3–12 and 18–29) or a homologous nucleic acid (SEQ ID NOs:30–46). In one aspect, the probe is a single stranded complementary RNA or DNA molecule.

The invention further provides a method for detecting a nucleic acid molecule in a sample, the method comprising the steps of hybridizing a probe to at least one nucleic acid molecule of a sample, forming a hybridization complex; and detecting the hybridization complex, wherein the presence of the hybridization complex indicates the presence of the nucleic acid molecule in the sample. In one aspect, the method further comprises amplifying the nucleic acid molecule prior to hybridization. The nucleic acid molecule or a fragment thereof may comprise either an element or a target on a microarray.

The invention also provides a method for using a nucleic acid molecule or a fragment thereof to screen a library of molecules to identify at least one ligand which specifically binds the nucleic acid molecule, the method comprising combining the nucleic acid molecule with a library of molecules under conditions allowing specific binding, and detecting specific binding, thereby identifying a ligand which specifically binds the nucleic acid molecule. Such libraries include DNA and RNA molecules, peptides, PNAs, proteins, and the like. In an analogous method, the nucleic acid molecule or a fragment thereof is used to purify a ligand.

The invention also provides an expression vector containing at least a fragment of the nucleic acid molecule. In another aspect, the expression vector is contained within a host cell. The invention further provides a method for producing a protein, the method comprising the steps of culturing the host cell under conditions for the expression of the protein and recovering the protein from the host cell culture.

The invention also provides a substantially purified mammalian imidazoline receptor or a portion thereof. The invention further provides isolated and purified proteins having the amino acid sequences of SEQ ID NO:2. Additionally, the invention provides a pharmaceutical composition comprising a substantially purified mammalian protein or a portion thereof in conjunction with a pharmaceutical carrier.

The invention further provides a method for using at least a portion of the mammalian protein to produce antibodies. The invention also provides a method for using a mammalian protein or a portion thereof to screen a library of molecules to identify at least one ligand which specifically binds the protein, the method comprising combining the protein with the library of molecules under conditions allowing specific binding, and detecting specific binding, thereby identifying a ligand which specifically binds the protein. Such libraries include DNA and RNA molecules, peptides, agonists, antagonists, antibodies, immunoglobulins, drug compounds, pharmaceutical agents, and other ligands. In one aspect, the ligand identified using the method modulates the activity of the mammalian protein. In an analogous method, the protein or a portion thereof is used to purify a ligand. The method involves combining the mammalian protein or a portion thereof with a sample under conditions to allow specific binding, detecting specific binding between the protein and ligand, recovering the bound protein, and separating the protein from the ligand to obtain purified ligand.

The invention further provides a method for inserting a marker gene into the genomic DNA of a mammal to disrupt the expression of the natural mammalian nucleic acid molecule. The invention also provides a method for using the mammalian nucleic acid molecule to produce a mammalian model system, the method comprising constructing a vector containing the mammalian nucleic acid molecule; introducing the vector into a totipotent mammalian embryonic stem cell; selecting an embryonic stem cell with the vector integrated into genomic DNA; microinjecting the selected cell into a mammalian blastocyst, thereby forming a chimeric blastocyst; transferring the chimeric blastocyst into a pseudopregnant dam, wherein the dam gives birth to a chimeric mammal containing at least one additional copy of mammalian nucleic acid molecule in its germ line; and breeding the chimeric mammal to generate a homozygous mammalian model system.

BRIEF DESCRIPTION OF THE FIGURES AND TABLE

FIGS. 1A, 1B, 1C, 1D, 1E, 1F, 1G, 1H, 1I, 1J, 1K, 1L, 1M, and 1N show the mammalian nucleic acid molecule (SEQ ID NO: 1) encoding the amino acid sequence (SEQ ID NO:2) of the mammalian protein. The alignment was produced using MACDNASIS PRO software (Hitachi Software Engineering, South San Francisco Calif.).

FIGS. 2A, 2B, 2C, 2D, 2E, 2F, and 2G demonstrate the chemical and structural similarity between mIR (129581; SEQ ID NO:2) and human imidazoline receptor subtype 1 (GENESEQ W43396; SEQ ID NO:47), produced using the LASERGENE software (DNASTAR, Madison Wis.).

Table 1 compares Incyte human, monkey, mouse, and rat nucleic acid molecules as shown by SEQ ID NO, Incyte clone number, clone length in nucleotides, tissue source, Incyte cDNA library name, region of overlap with nucleotides of SEQ ID NO:1, and percent identity with SEQ ID NO:1 calculated using LASERGENE software (DNASTAR).

DESCRIPTION OF THE INVENTION

It is understood that this invention is not limited to the particular machines, materials and methods described. It is also to be understood that the terminology used herein is for the purpose of describing particular embodiments only and is not intended to limit the scope of the present invention which will be limited only by the appended claims. As used herein, the singular forms "a," "an," and "the" include plural reference unless the context clearly dictates otherwise. For example, a reference to "a host cell" includes a plurality of such host cells known to those skilled in the art.

Unless defined otherwise, all technical and scientific terms used herein have the same meanings as commonly understood by one of ordinary skill in the art to which this invention belongs. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"Mammalian imidazoline receptor (mIR)" refers to a substantially purified protein obtained from any mammalian species, including bovine, ovine, porcine, rodent, canine, simian, and preferably the human species, and from any source, whether natural, synthetic, semi-synthetic, or recombinant.

"Biologically active" refers to a protein having structural, immunological, regulatory, or chemical functions of a naturally occurring, recombinant or synthetic molecule.

"Complementary" refer to the natural hydrogen bonding by base pairing between purines and pyrimidines. For example, the sequence A-C-G-T forms hydrogen bonds with its complements T-G-C-A or U-G-C-A. Two single-stranded molecules may be considered partially complementary, if only some of the nucleotides bond, or completely complementary, if nearly all of the nucleotides bond. The degree of complementarity between nucleic acid strands affects the efficiency and strength of the hybridization and amplification reactions.

"Derivative" refers to the chemical modification of a nucleic acid molecule or amino acid sequence. Chemical modifications can include replacement of hydrogen by an alkyl, acyl, or amino group or glycosylation, pegylation, or any similar process which retains or enhances biological activity or lifespan of the molecule or sequence.

"Fragment" refers to an Incyte clone or any part of a nucleic acid molecule which retains a usable, functional characteristic. Useful fragments include oligonucleotides which may be used in hybridization or amplification technologies or in regulation of replication, transcription or translation.

"Hybridization complex" refers to a complex between two nucleic acid molecules by virtue of the formation of hydrogen bonds between purines and pyrimidines.

"Ligand" refers to any molecule, agent, or compound which will bind specifically to a complementary site on a nucleic acid molecule or protein. Such ligands stabilize or modulate the activity of nucleic acid molecules or proteins of the invention and may be composed of at least one of the following: inorganic and organic substances including nucleic acids, proteins, carbohydrates, fats, and lipids.

"Modulates" refers to a change in activity (biological, chemical, or immunological) or lifespan resulting from specific binding between a molecule and either a nucleic acid molecule or a protein.

"Nucleic acid molecule" refers to a nucleic acid, oligonucleotide, nucleotide, polynucleotide or any fragment thereof. It may be DNA or RNA of genomic or synthetic origin, double-stranded or single-stranded, and combined with carbohydrate, lipids, protein or other materials to perform a particular activity such as transformation or form a useful composition such as a peptide nucleic acid (PNA). "Oligonucleotide" is substantially equivalent to the terms amplimer, primer, oligomer, element, target, and probe and is preferably single stranded.

"Protein" refers to an amino acid sequence, oligopeptide, peptide, polypeptide or portions thereof whether naturally occurring or synthetic.

"Portion", as used herein, refers to any part of a protein used for any purpose, but especially for the screening of a library of molecules or compounds to identify molecules which specifically bind to that portion or for the production of antibodies.

"Sample" is used in its broadest sense. A sample containing nucleic acid molecules may comprise a bodily fluid; an extract from a cell, chromosome, organelle, or membrane isolated from a cell; genomic DNA, RNA, or cDNA in solution or bound to a substrate; a cell; a tissue; a tissue print; and the like.

"Substantially purified" refers to nucleic acid molecules or proteins that are removed from their natural environment and are isolated or separated, and are at least about 60% free, preferably about 75% free, and most preferably about 90% free, from other components with which they are naturally associated.

"Substrate" refers to any rigid or semi-rigid support to which nucleic acid molecules or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

THE INVENTION

The invention is based on the discovery of a new mammalian nucleic acid molecule which encodes a mammalian imidazoline receptor (mIR), and on the use of the nucleic acid molecule, or fragments thereof, and protein, or portions thereof, as compositions in the characterization, diagnosis, treatment, or prevention of conditions such as hypertension, cancer, immune, and reproductive disorders.

Nucleic acids encoding mIR of the present invention were first identified in the ZOOSEQ database using the Library Comparisons software program (ZOOSEQ database, Incyte Pharmaceuticals, Palo Alto Calif.). The master cluster which included Incyte clone number 700230141H1 (SEQ ID NO:43) from the rat colon tissue library (RACONOT01) was present only in streptozotocin-treated rat spinal cord tissue and aligned with the polynucleotide encoding human imidazoline receptor subtype 1 (I-IR; W43396; SEQ ID NO:47). Following electronic assemblage with clones in the ZOOSEQ database (Incyte Pharmaceuticals), Incyte clone number 700230141H1 was used to identify human sequences in the LIFESEQ database (Incyte Pharmaceuticals) using BLAST analysis. Incyte clone number 700230141, designated as rat mIR (rIR; SEQ ID NO:43) was used to identify homologous imidazoline receptor sequences in the Incyte LIFESEQ database (Incyte Pharmaceuticals). These sequences, Incyte clones (libraries): 3276916H1 (PROSBPT06), 2431638H1 (EOSINOT03), 2263366X12F1 (UTRSNOT02), 2526601F6 (BRAITUT21), 4031726H1 (BRAINOT23), 4014626F6 (BRAXNOT01), 2263366X16F1 (UTRSNOT02), 2488189F6 (LUNGNOT22), 4014626T6 (BRAXNOT01), 2309651H1(NGANNOT01), 1659790H1 (URETTUT01), 5505610H1 (BRADDIR01), 4745071H1 (BRAWNOT01), 4640790H1 (PROSTMT03), 3087155F6 (HEAONOT03), 4834547H1 (BRAWNOT01), 2482087H1 (SMCANOT01), 396596H1 (PITUNOT02), 2300531 R6 (BRSTNOT05), 2858139F6 (SININOT03), 2096273R6 (BRAITUT02), 2521806H1 (BRAITUT21), 1886951F6 (BLADTUT07), 2204546H1 (SPLNFET02), 1540117R1 (SINTTUT01), 1724089F6 (PROSNOT14), and 1809315F6 (PROSTUT12), SEQ ID NOs:3–29, respectively, contributed to the assembly of the consensus sequence, SEQ ID NO: 1, which encodes mIR, as shown in FIGS. 1A–1N, and Table 1.

Northern analysis shows expression of mIR in various libraries, particularly heavily vascularized (77%), reproductive (28%), nervous (25%) and developmental (9%) tissues. SEQ ID NO:1 is present in 65% of cancerous or proliferating tissues and in 28% of inflamed, immune responsive, or infected tissues.

mIR comprising the amino acid sequence of SEQ ID NO:2 is 1504 amino acids in length and has a potential N-glycosylation site at residue N 1298; one potential cAMP- and cGMP-dependent protein kinase phosphorylation site at residue R11035; twenty three potential casein kinase II phosphorylation sites at residues S83, S193, S225, S253, S263, T273, T290, S298, S300, S345, T443, S467, S524, T598 S830, S1004, S1026, T1090, T1115, S1149, S1277, S1321, and T1376; seventeen potential protein kinas phosphorylation sites at residues T3, T45, T107, T184, S246, S253, S305, T443, S721, S756, S863, S940, S1130, S1136, S1183, T1301, and S1312; one potential tyrosine kinase phosphorylation site at residue Y95; a leucine zipper pattern between residues L694 and L715; three leucine-rich repeat PFAM signatures from residue A288 to Y332, N333 to Y377, and S378 to A426, respectively; a PhoX homologous domain between residues E14 and H118; and a cytochrome P450 cysteine heme-iron ligand signature between residues F803 and A812. BLOCKS DOMO identifies two leucine-rich repeats from L328 to L339 and L351 to L362; a pyruvate (flavodoxin) domain from L972 to Q1024; a nitrate transport domain between L506 to E516; PFAM identifies two SP1a and the RYanodine receptor domains at E637 to A650 and Y978 to N999, respectively, and a Disheveled and axin domain at P492 to D527; and PRINTS identifies three leucine-rich repeat signatures: L334 to L347; L289 to 1302; and L331 to L344. FIGS. 2A, 2B, 2C, 2D, 2E, 2F, and 2G demonstrate the chemical and structural similarity between mIR (SEQ ID NO:2) and human imidazoline receptor subtype 1 (Genseq W43396; SEQ ID NO:47). The amino acids of SEQ ID NO:2, from residue L70 to residue D91 or from residue L161 to residue L177 are particularly appropriate for antibody production. The regions of SEQ ID NO:1 from nucleotide 1 through 1424 and from nucleotide 2311 through 5128 represent a variant of the imidazoline receptor subtype 1 (SEQ ID NO:47).

The nucleic acid molecule, SEQ ID NO:1, encoding mIR of the present invention was used to identify homologous clones in the ZOOSEQ database (Incyte Pharmaceuticals) using BLAST analysis. Clones from various monkey libraries: 700708590H1 (MNBFNOT01), 700720751H1 (MNBFNOT01), 700705986H1 (MNBFNOT01); various mouse libraries: 701251065H1 (MOLUDIT07), 701087190H1 (MOLUDIT05); and from various rat libraries: 700057363H1 (RASPNOT01), 700068150H1 (RABTNOT01), 700230141H1 (RACONOT01), 70027887H1 (RATONOT02), 700292102H1 (RAEPNOT01), 700329107H1 (RALINON04), 700514583H1 (RASNNOT01), 700768834H1 (RAHYNOT02), 700810051H1 (RAPINOT03), 701024483H1 (RAFANOT02), 701273187H1 (RABXNOT01), 701289331H1 (RABXNOT03); SEQ ID NOs:30–46, respectively, were identified and are shown in Table 1.

The nucleic acid sequence, SEQ ID NO:1, and fragments and variants thereof (SEQ ID NOs:3–46) may be used in hybridization and amplification technologies to identify and distinguish among SEQ ID NO:1 and similar molecules in a sample. The molecules may be used to mimic human conditions, diseases, or disorders, produce transgenic animal models for these conditions, or to monitor animal toxicology studies, clinical trials, and subject/patient treatment profiles.

Characterization and Use of the Invention
cDNA libraries

In a particular embodiment disclosed herein, mRNA was isolated from mammalian cells and tissues using methods which are well known to those skilled in the art and used to prepare the cDNA libraries. The Incyte clones listed above were isolated from mammalian cDNA libraries. At least one library preparation representative of the invention is described in the EXAMPLES below. The consensus mammalian sequences were chemically and/or electronically assembled from fragments including Incyte clones and extension and/or shotgun sequences using computer programs such as Phrap (P. Green, University of Washington, Seattle Wash.), GELVIEW Fragment Assembly system (Genetics Computer Group, Madison Wis.), and AUTOASSEMBLER application (PE Biosystems, Foster City Calif.). Clones, extension and/or shotgun sequences are electronically assembled into clusters and/or master clusters.

Sequencing

Methods for sequencing nucleic acids are well known in the art and may be used to practice any of the embodiments of the invention. These methods employ enzymes such as the Klenow fragment of DNA polymerase I, SEQUENASE, Taq DNA polymerase and thermostable T7 DNA polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the HYDRA microdispenser (Robbins Scientific, Sunnyvale Calif.), MICROLAB 2200 system (Hamilton, Reno Nev.), and the DNA ENGINE thermal cycler (PTC200; MJ Research, Watertown Mass.). Machines used for sequencing include the ABI PRISM 3700, 377 or 373 DNA sequencing systems (PE Biosystems), the MEGABACE 1000 DNA sequencing system (Amersham Pharmacia Biotech), and the like. The sequences may be analyzed using a variety of algorithms which are well known in the art and described in Ausubel et al. (1997; *Short Protocols in Molecular Biology*, John Wiley & Sons, New York N.Y., unit 7.7) and Meyers (1995; *Molecular Biology and Biotechnology*, Wiley VCH, New York N.Y., pp. 856–853).

Shotgun sequencing is used to generate more sequence from cloned inserts derived from multiple sources. Shotgun sequencing methods are well known in the art and use thermostable DNA polymerases, heat-labile DNA polymerases, and primers chosen from representative regions flanking the nucleic acid molecules of interest. Incomplete assembled sequences are inspected for identity using various algorithms or programs such as CONSED (Gordon (1998) Genome Res. 8:195–202) which are well known in the art. Contaminating sequences including vector or chimeric sequences or deleted sequences can be removed or restored, respectively, organizing the incomplete assembled sequences into finished sequences.

Extension of a Nucleic Acid Sequence

The sequences of the invention may be extended using various PCR-based methods known in the art. For example, the XL-PCR kit (PE Biosystems), nested primers, and commercially available cDNA or genomic DNA libraries may be used to extend the nucleic acid sequence. For all PCR-based methods, primers may be designed using commercially available software, such as OLIGO 4.06 primer analysis software (National Biosciences, Plymouth Minn.) to be about 22 to 30 nucleotides in length, to have a GC content of about 50% or more, and to anneal to a target molecule at temperatures from about 55° C. to about 68° C. When extending a sequence to recover regulatory elements, it is preferable to use genomic, rather than cDNA libraries.

Use of the Mammalian Nucleic Acid Molecule

Hybridization

The mammalian nucleic acid molecule and fragments thereof can be used in hybridization technologies for various purposes. A probe may be designed or derived from unique regions such as the 5' regulatory region or from a conserved motif such as the imidazoline receptor signature and used in protocols to identify naturally occurring molecules encoding the mammalian protein, allelic variants, or related molecules. The probe may be DNA or RNA, is usually single stranded and should have at least 50% sequence identity to any of the nucleic acid sequences. Hybridization probes may be produced using oligolabeling, nick translation, end-labeling, or PCR amplification in the presence of labeled nucleotide. A vector containing the nucleic acid molecule or a fragment thereof may be used to produce an mRNA probe in vitro by addition of an RNA polymerase and labeled nucleotides. These procedures may be conducted using commercially available kits such as those provided by Amersham Pharmacia Biotech.

The stringency of hybridization is determined by G+C content of the probe, salt concentration, and temperature. In particular, stringency can be increased by reducing the concentration of salt or raising the hybridization temperature. In solutions used for some membrane based hybridizations, addition of an organic solvent such as formamide allows the reaction to occur at a lower temperature. Hybridization can be performed at low stringency with buffers, such as 5×SSC with 1% sodium dodecyl sulfate (SDS) at 60° C., which permits the formation of a hybridization complex between nucleic acid sequences that contain some mismatches. Subsequent washes are performed at higher stringency with buffers such as 0.2×SSC with 0.1% SDS at either 45° C. (medium stringency) or 68° C. (high stringency). At high stringency, hybridization complexes will remain stable only where the nucleic acid molecules are completely complementary. In some membrane-based hybridizations, preferably 35% or most preferably 50%, formamide can be added to the hybridization solution to reduce the temperature at which hybridization is performed, and background signals can be reduced by the use of other detergents such as Sarkosyl or Triton X-100 and a blocking agent such as denatured salmon sperm DNA. Selection of components and conditions for hybridization are well known to those skilled in the art and are reviewed in Ausubel (supra) and Sambrook et al. (1989) *Molecular Cloning A Laboratory Manual*, Cold Spring Harbor Press, Plainview N.Y.

Microarrays may be prepared and analyzed using methods known in the art. Oligonucleotides may be used as either probes or targets in a microarray. The microarray can be used to monitor the expression level of large numbers of genes simultaneously and to identify genetic variants, mutations, and single nucleotide polymorphisms. Such information may be used to determine gene function; to understand the genetic basis of a condition, disease, or disorder; to diagnose a condition, disease, or disorder; and to develop and monitor the activities of therapeutic agents. (See, e.g., Brennan et al. (1995) U.S. Pat. No. 5,474,796; Schena et al. (1996) Proc. Natl. Acad. Sci. 93:10614–10619; Baldeschweiler et al. (1995) PCT application WO95/251116; Shalon et al. (1995) PCT application WO95/35505; Heller et al. (1997) Proc. Natl. Acad. Sci. 94:2150–2155; and Heller et al. (1997) U.S. Pat. No. 5,605,662.)

Hybridization probes are also useful in mapping the naturally occurring genomic sequence. The probes may be hybridized to: 1) a particular chromosome, 2) a specific region of a chromosome, or 3) artificial chromosome construction such as human artificial chromosome (HAC), yeast artificial chromosome (YAC), bacterial artificial chromosome (BAC), bacterial P1 construction, or single chromosome cDNA libraries.

Expression

A multitude of nucleic acid molecules encoding mIR may be cloned into a vector and used to express the protein, or portions thereof, in host cells. The nucleic acid sequence can be engineered by such methods as DNA shuffling (Stemmer and Crameri (1996) U.S. Pat. No. 5,830,721 incorporated by reference herein) and site-directed mutagenesis to create new restriction sites, alter glycosylation patterns, change codon preference to increase expression in a particular host, produce splice variants, extend half-life, and the like. The expression vector may contain transcriptional and translational control elements (promoters, enhancers, specific initiation signals, and polyadenylated 3' sequence) from various sources which have been selected for their efficiency in a particular host. The vector, nucleic acid molecule, and regulatory elements are combined using in vitro recombinant DNA techniques, synthetic techniques, and/or in vivo genetic recombination techniques well known in the art and described in Sambrook (supra, ch. 4, 8, 16 and 17).

A variety of host systems may be transformed with an expression vector. These include, but are not limited to, bacteria transformed with recombinant bacteriophage, plasmid, or cosmid DNA expression vectors; yeast transformed with yeast expression vectors; insect cell systems transformed with baculovirus expression vectors; plant cell systems transformed with expression vectors containing viral and/or bacterial elements, or animal cell systems (Ausubel supra, unit 16). For example, an adenovirus transcription/translation complex may be utilized in mammalian cells. After sequences are ligated into the E1 or E3 region of the viral genome, the infective virus is used to transform and express the protein in host cells. The Rous sarcoma virus enhancer or SV40 or EBV-based vectors may also be used for high-level protein expression.

Routine cloning, subcloning, and propagation of nucleic acid sequences can be achieved using the multifunctional PBLUESCRIPT vector (Stratagene, La Jolla Calif.) or PSPORT1 plasmid (Life Technologies). Introduction of a nucleic acid sequence into the multiple cloning site of these vectors disrupts the lacZ gene and allows calorimetric screening for transformed bacteria. In addition, these vectors may be useful for in vitro transcription, dideoxy sequencing, single strand rescue with helper phage, and creation of nested deletions in the cloned sequence.

For long term production of recombinant proteins, the vector can be stably transformed into cell lines along with a selectable or visible marker gene on the same or on a separate vector. After transformation, cells are allowed to grow for about 1 to 2 days in enriched media and then are transferred to selective media. Selectable markers, antimetabolite, antibiotic, or herbicide resistance genes, confer resistance to the relevant selective agent and allow growth and recovery of cells which successfully express the introduced sequences. Resistant clones identified either by survival on selective media or by the expression of visible markers, such as anthocyanins, green fluorescent protein (GFP),β glucuronidase, luciferase and the like, may be propagated using culture techniques. Visible markers are also used to quantify the amount of protein expressed by the introduced genes. Verification that the host cell contains the desired mammalian nucleic acid molecule is based on DNA-DNA or DNA-RNA hybridizations or PCR amplification techniques.

The host cell may be chosen for its ability to modify a recombinant protein in a desired fashion. Such modifications include acetylation, carboxylation, glycosylation, phosphorylation, lipidation, acylation and the like. Post-translational processing which cleaves a "prepro" form may also be used to specify protein targeting, folding, and/or activity. Different host cells available from the ATCC (Bethesda, Md.) which have specific cellular machinery and characteristic mechanisms for post-translational activities may be chosen to ensure the correct modification and processing of the recombinant protein.

Recovery of Proteins from Cell Culture

Heterologous moieties engineered into a vector for ease of purification include glutathione S-transferase (GST), calmodulin binding peptide (CBP), 6-His, FLAG, MYC, and the like. GST, CBP, and 6-His are purified using commercially available affinity matrices such as immobilized glutathione, calmodulin, and metal-chelate resins, respectively. FLAG and MYC are purified using commercially available monoclonal and polyclonal antibodies. A proteolytic cleavage site may be located between the desired protein sequence and the heterologous moiety for ease of separation following purification. Methods for recombinant protein expression and purification are discussed in Ausubel (supra, unit 16) and are commercially available.

Chemical Synthesis of Peptides

Proteins or portions thereof may be produced not only by recombinant methods, but also by using chemical methods well known in the art. Solid phase peptide synthesis may be carried out in a batchwise or continuous flow process which sequentially adds α-amino- and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-α-protected by acid labile Boc (t-butyloxycarbonyl) or base-labile Fmoc(9-fluorenylmethoxycarbonyl). The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full length peptide is synthesized by sequential deprotection, coupling of derivitized amino acids, and washing with dichloromethane and/or N,N-dimethylformamide. The peptide is cleaved between the peptide carboxy terminus and the linker group to yield a peptide acid or amide. (Novabiochem 1997/98 Catalog and Peptide Synthesis Handbook, San Diego Cailf. pp. S1–20). Automated synthesis may also be carried out on machines such as the ABI 431A peptide synthesizer (PE Biosystems). A protein or portion thereof may be substantially purified by preparative high performance liquid chromatography and its composition confirmed by amino acid analysis or by sequencing (Creighton (1984) *Proteins, Structures and Molecular Properties,* WH Freeman, New York N.Y.).

Preparation and Screening of Antibodies

Various hosts including goats, rabbits, rats, mice, humans, and others may be immunized by injection with mIR or any portion thereof. Adjuvants such as Freund's, mineral gels, and surface active substances such as lysolecithin, pluronic polyols, polyanions, peptides, oil emulsions, keyhole limpet hemacyanin (KLH), and dinitrophenol may be used to increase immunological response. The oligopeptide, peptide, or portion of protein used to induce antibodies should consist of at least about five amino acids, more preferably ten amino acids, which are identical to a portion of the natural protein. Oligopeptides may be fused with proteins such as KLH in order to produce antibodies to the chimeric molecule.

Monoclonal antibodies may be prepared using any technique which provides for the production of antibodies by continuous cell lines in culture. These include, but are not limited to, the hybridoma technique, the human B-cell hybridoma technique, and the EBV-hybridoma technique. (See, e.g., Kohler et al. (1975) Nature 256:495–497; Kozbor et al. (1985) J. Immunol. Methods 81:31–42; Cote et al. (1983) Proc. Natl. Acad. Sci. 80:2026–2030; and Cole et al. (1984) Mol. Cell Biol. 62:109–120.)

Alternatively, techniques described for the production of single chain antibodies may be adapted, using methods known in the art, to produce epitope specific single chain antibodies. Antibody fragments which contain specific binding sites for epitopes of the mammalian protein may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse et al. (1989) Science 246:1275–1281.)

The mammalian protein or a portion thereof may be used in screening assays of phagemid or B-lymphocyte immunoglobulin libraries to identify antibodies having the desired specificity. Numerous protocols for competitive binding or immunoassays using either polyclonal or monoclonal antibodies with established specificities are well known in the art. Such immunoassays typically involve the measurement of complex formation between the protein and its specific antibody. A two-site, monoclonal-based immunoassay utilizing monoclonal antibodies reactive to two non-interfering epitopes is preferred, but a competitive binding assay may also be employed (Pound (1998) *Immunochemical Protocols*, Humana Press, Totowa N.J.).

Labeling of Molecules for Assay

A wide variety of labels and conjugation techniques are known by those skilled in the art and may be used in various nucleic acid, amino acid, and antibody assays. Synthesis of labeled molecules may be achieved using Promega (Madison Wis.) or Amersham Pharmacia Biotech kits for incorporation of a labeled nucleotide such as $^{32}$P-dCTP, Cy3-dCTP or Cy5-dCTP or amino acid such as $^{35}$S-methionine. Nucleotides and amino acids may be directly labeled with a variety of substances including fluorescent, chemiluminescent, or chromogenic agents, and the like, by chemical conjugation to amines, thiols and other groups present in the molecules using reagents such as BIODIPY or FITC (Molecular Probes, Eugene Oreg.).

Diagnostics

The nucleic acid molecules, fragments, oligonucleotides, complementary RNA and DNA molecules, and PNAs may be used to detect and quantify altered gene expression, absence/presence vs. excess, expression of mRNAs or to monitor mRNA levels during therapeutic intervention. Conditions, diseases or disorders associated with altered expression include acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, benign prostatic hyperplasia, bronchitis, Chediak-Higashi syndrome, cholecystitis, Crohn's disease, atopic dermatitis, dermatomyositis, diabetes mellitus, emphysema, erythroblastosis fetalis, erythema nodosum, atrophic gastritis, glomerulonephritis, Goodpasture's syndrome, gout, chronic granulomatous diseases, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polycystic ovary syndrome, polymyositis, psoriasis, Reiter's syndrome, rheumatoid arthritis, scleroderma, severe combined immunodeficiency disease (SCID), Sjögren's syndrome, systemic anaphylaxis, systemic lupus erythematosus, systemic sclerosis, thrombocytopenic purpura, ulcerative colitis, uveitis, Werner syndrome, hemodialysis, extracorporeal circulation, viral, bacterial, fungal, parasitic, protozoal, and helminthic infection; a disorder of prolactin production, infertility, including tubal disease, ovulatory defects, and endometriosis, a disruption of the estrous cycle, a disruption of the menstrual cycle, polycystic ovary syndrome, ovarian hyperstimulation syndrome, an endometrial or ovarian tumor, a uterine fibroid, autoimmune disorders, an ectopic pregnancy, and teratogenesis; cancer of the breast, fibrocystic breast disease, and galactorrhea; a disruption of spermatogenesis, abnormal sperm physiology, benign prostatic hyperplasia, prostatitis, Peyronie's disease, impotence, gynecomastia; actinic keratosis, arteriosclerosis, bursitis, cirrhosis, hepatitis, mixed connective tissue disease (MCTD), myelofibrosis, paroxysmal nocturnal hemoglobinuria, polycythemia vera, primary thrombocythemia, complications of cancer, cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. The diagnostic assay may use hybridization or amplification technology to compare gene expression in a biological sample from a patient to standard samples in order to detect altered gene expression. Qualitative or quantitative methods for this comparison are well known in the art.

For example, the nucleic acid molecule or probe may be labeled by standard methods and added to a biological sample from a patient under conditions for the formation of hybridization complexes. After an incubation period, the sample is washed and the amount of label (or signal) associated with hybridization complexes, is quantified and compared with a standard value. If the amount of label in the patient sample is significantly altered in comparison to the standard value, then the presence of the associated condition, disease or disorder is indicated.

In order to provide a basis for the diagnosis of a condition, disease or disorder associated with gene expression, a normal or standard expression profile is established. This may be accomplished by combining a biological sample taken from normal subjects, either animal or human, with a probe under conditions for hybridization or amplification. Standard hybridization may be quantified by comparing the values obtained using normal subjects with values from an experiment in which a known amount of a substantially purified target sequence is used. Standard values obtained in this manner may be compared with values obtained from samples from patients who are symptomatic for a particular condition, disease, or disorder. Deviation from standard values toward those associated with a particular condition is used to diagnose that condition.

Such assays may also be used to evaluate the efficacy of a particular therapeutic treatment regimen in animal studies and in clinical trial or to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to months.

Immunological Methods

Detection and quantification of a protein using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes is preferred, but a competitive binding assay may be employed. (See, e.g., Coligan et al. (1997) *Current Protocols in Immunology,* Wiley-Interscience, New York N.Y.; and Pound, supra.)

Therapeutics

Chemical and structural similarity, e.g., in the context of sequences and motifs, exists between regions of mIR (SEQ ID NO:2) and human imidazoline receptor subtype 1 (GENESEQ W43396; SEQ ID NO:47). In addition, gene expression is closely associated with vascularized, reproductive, and nervous tissues and appears to play a role in conditions such as hypertension, cancer, immune, and reproductive disorders. In the treatment of conditions associated with increased expression or activity, it is desirable to decrease expression or protein activity. In the treatment of conditions associated with decreased expression or activity, it is desirable to increase expression or protein activity.

In one embodiment, the mammalian protein or a portion or derivative thereof may be administered to a subject to treat or prevent a condition associated with altered expression or activity of the mammalian protein. Examples of such conditions include, but are not limited to, acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, benign prostatic hyperplasia, bronchitis, Chediak-Higashi syndrome, cholecystitis, Crohn's disease, atopic dermatitis, dermatomyositis, diabetes mellitus, emphysema, erythroblastosis fetalis, erythema nodosum, atrophic gastritis, glomerulonephritis, Goodpasture's syndrome, gout, chronic granulomatous diseases, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polycystic ovary syndrome, polymyositis, psoriasis, Reiter's syndrome, rheumatoid arthritis, scleroderma, severe combined immunodeficiency disease (SCID), Sjögren's syndrome, systemic anaphylaxis, systemic lupus erythematosus, systemic sclerosis, thrombocytopenic purpura, ulcerative colitis, uveitis, Werner syndrome, hemodialysis, extracorporeal circulation, viral, bacterial, fungal, parasitic, protozoal, and helminthic infection; a disorder of prolactin production, infertility, including tubal disease, ovulatory defects, and endometriosis, a disruption of the estrous cycle, a disruption of the menstrual cycle, polycystic ovary syndrome, ovarian hyperstimulation syndrome, an endometrial or ovarian tumor, a uterine fibroid, autoimmune disorders, an ectopic pregnancy, and teratogenesis; cancer of the breast, fibrocystic breast disease, and galactorrhea; a disruption of spermatogenesis, abnormal sperm physiology, benign prostatic hyperplasia, prostatitis, Peyronie's disease, impotence, gynecomastia; actinic keratosis, arteriosclerosis, bursitis, cirrhosis, hepatitis, mixed connective tissue disease (MCTD), myelofibrosis, paroxysmal nocturnal hemoglobinuria, polycythemia vera, primary thrombocythemia, complications of cancer, cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a pharmaceutical composition comprising a substantially purified mammalian protein in conjunction with a pharmaceutical carrier may be administered to a subject to treat or prevent a condition associated with altered expression or activity of the endogenous protein including, but not limited to, those provided above.

In a further embodiment, a ligand which modulates the activity of the mammalian protein may be administered to a subject to treat or prevent a condition associated with altered lifespan, expression, or activity of the protein including, but not limited to, those listed above. In one aspect, an antibody which specifically binds the mammalian protein may be used as a targeting or delivery mechanism for bringing a pharmaceutical agent to cells or tissue which express the mammalian protein.

In an additional embodiment, a vector capable of expressing the mammalian protein or a portion or derivative thereof may be administered to a subject to treat or prevent a condition associated with altered lifespan, expression, or activity of protein including, but not limited to, those described above.

In a still further embodiment, a vector expressing the complement of the nucleic acid molecule or fragments thereof may be administered to a subject to treat or prevent a condition associated with altered lifespan, expression, or activity of the protein including, but not limited to, those described above.

Any of the nucleic acid molecules, complementary molecules and fragments thereof, proteins or portions thereof, vectors delivering these nucleic acid molecules or proteins, and their ligands may be administered in combination with other therapeutic agents. Selection of the agents for use in combination therapy may be made by one of ordinary skill in the art according to conventional pharmaceutical principles. A combination of therapeutic agents may act synergistically to effect prevention or treatment of a particular condition at a lower dosage of each agent.

Modification of Gene Expression Using Nucleic Acids

Gene expression may be modified by designing complementary or antisense molecules (DNA, RNA, or PNA) to the control, 5', 3', or other regulatory regions of the mammalian gene. Oligonucleotides designed with reference to the transcription initiation site are preferred. Similarly, inhibition can be achieved using triple helix base-pairing which inhibits the binding of polymerases, transcription factors, or regulatory molecules (Gee et al. In: Huber and Carr (1994) *Molecular and Immunologic Approaches,* Futura Publishing, Mt. Kisco N.Y., pp. 163–177). A complementary molecule may also be designed to block translation by preventing binding between ribosomes and mRNA. In one alternative, a library of nucleic acid molecules or fragments thereof may be screened to identify those which specifically bind a regulatory, nontranslated sequence.

Ribozymes, enzymatic RNA molecules, may also be used to catalyze the specific cleavage of RNA. The mechanism of ribozyme action involves sequence-specific hybridization of the ribozyme molecule to complementary target RNA followed by endonucleolytic cleavage at sites such as GUA, GUU, and GUC. Once such sites are identified, an oligonucleotide with the same sequence may be evaluated for secondary structural features which would render the oligonucleotide inoperable. The suitability of candidate targets may also be evaluated by testing their hybridization with complementary oligonucleotides using ribonuclease protection assays.

Complementary nucleic acids and ribozymes of the invention may be prepared via recombinant expression, in vitro or in vivo, or using solid phase phosphoramidite chemical synthesis. In addition, RNA molecules may be modified to increase intracellular stability and half-life by addition of flanking sequences at the 5' and/or 3' ends of the molecule or by the use of phosphorothioate or 2'O-methyl rather than phosphodiesterase linkages within the backbone of the molecule. Modification is inherent in the production of PNAs and can be extended to other nucleic acid molecules. Either the inclusion of nontraditional bases such as inosine, queosine, and wybutosine, and or the modification of adenine, cytidine, guanine, thymine, and uridine with acetyl-, methyl-, thio- groups renders the molecule less available to endogenous endonucleases.

Screening Assays

The nucleic acid molecule encoding the mammalian protein may be used to screen a library of molecules or compounds for specific binding affinity. The libraries may be DNA molecules, RNA molecules, PNAs, peptides, proteins such as transcription factors, enhancers, repressors, and other ligands which regulate the activity, replication, transcription, or translation of the nucleic acid molecule in the biological system. The assay involves combining the mammalian nucleic acid molecule or a fragment thereof with the library of molecules under conditions allowing specific binding, and detecting specific binding to identify at least one molecule which specifically binds the nucleic acid molecule.

Similarly the mammalian protein or a portion thereof may be used to screen libraries of molecules or compounds in any of a variety of screening assays. The portion of the protein employed in such screening may be free in solution, affixed to an abiotic or biotic substrate (e.g. borne on a cell surface), or located intracellularly. Specific binding between the protein and molecule may be measured. Depending on the kind of library being screened, the assay may be used to identify DNA, RNA, or PNA molecules, agonists, antagonists, antibodies, immunoglobulins, inhibitors, peptides, proteins, drugs, or any other ligand, which specifically binds the protein. One method for high throughput screening using very small assay volumes and very small amounts of test compound is described in U.S. Pat. No. 5,876,946, incorporated herein by reference, which screens large numbers of molecules for enzyme inhibition or receptor binding.

Purification of Ligand

The nucleic acid molecule or a fragment thereof may be used to purify a ligand from a sample. A method for using a mammalian nucleic acid molecule or a fragment thereof to purify a ligand would involve combining the nucleic acid molecule or a fragment thereof with a sample under conditions to allow specific binding, detecting specific binding, recovering the bound protein, and using an appropriate agent to separate the nucleic acid molecule from the purified ligand.

Similarly, the protein or a portion thereof may be used to purify a ligand from a sample. A method for using a mammalian protein or a portion thereof to purify a ligand would involve combining the protein or a portion thereof with a sample under conditions to allow specific binding, detecting specific binding between the protein and ligand, recovering the bound protein, and using an appropriate chaotropic agent to separate the protein from the purified ligand.

Pharmacology

Pharmaceutical compositions are those substances wherein the active ingredients are contained in an effective amount to achieve a desired and intended purpose. The determination of an effective dose is well within the capability of those skilled in the art. For any compound, the therapeutically effective dose may be estimated initially either in cell culture assays or in animal models. The animal model is also used to achieve a desirable concentration range and route of administration. Such information may then be used to determine useful doses and routes for administration in humans.

A therapeutically effective dose refers to that amount of protein or inhibitor which ameliorates the symptoms or condition. Therapeutic efficacy and toxicity of such agents may be determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, and it may be expressed as the ratio, LD50/ED50. Pharmaceutical compositions which exhibit large therapeutic indexes are preferred. The data obtained from cell culture assays and animal studies are used in formulating a range of dosage for human use.

Model Systems

Animal models may be used as bioassays where they exhibit a toxic response similar to that of humans and where exposure conditions are relevant to human exposures. Mammals are the most common models, and most toxicity studies are performed on rodents such as rats or mice because of low cost, availability, and abundant reference toxicology. Inbred rodent strains provide a convenient model for investigation of the physiological consequences of under- or overexpression of genes of interest and for the development of methods for diagnosis and treatment of diseases. A mammal inbred to over-express a particular gene (for example, secreted in milk) may also serve as a convenient source of the protein expressed by that gene.

Toxicology

Toxicology is the study of the effects of agents on living systems. The majority of toxicity studies are performed on rats or mice to help predict the effects of these agents on human health. Observation of qualitative and quantitative changes in physiology, behavior, homeostatic processes, and lethality are used to generate a toxicity profile and to assess the consequences on human health following exposure to the agent.

Genetic toxicology identifies and analyzes the ability of an agent to produce genetic mutations. Genotoxic agents usually have common chemical or physical properties that facilitate interaction with nucleic acids and are most harmful when chromosomal aberrations are passed along to progeny.

Toxicological studies may identify agents that increase the frequency of structural or functional abnormalities in progeny if administered to either parent before conception, to the mother during pregnancy, or to the developing organism. Mice and rats are most frequently used in these tests because of their short reproductive cycle which produces the number of organisms needed to satisfy statistical requirements.

Acute toxicity tests are based on a single administration of the agent to the subject to determine the symptomology or lethality of the agent. Three experiments are conducted: 1) an initial dose-range-finding experiment, 2) an experiment to narrow the range of effective doses, and 3) a final experiment for establishing the dose-response curve.

Prolonged toxicity tests are based on the repeated administration of the agent. Rat and dog are commonly used in these studies to provide data from species in different families. With the exception of carcinogenesis, there is considerable evidence that daily administration of an agent at high-dose concentrations for periods of three to four months will reveal most forms of toxicity in adult animals.

Chronic toxicity tests, with a duration of a year or more, are used to demonstrate either the absence of toxicity or the carcinogenic potential of an agent. When studies are conducted on rats, a minimum of three test groups plus one control group are used, and animals are examined and monitored at the outset and at intervals throughout the experiment.

Transgenic Animal Models

Transgenic rodents which over-express or under-express a gene of interest may be inbred and used to model human diseases or to test therapeutic or toxic agents. (See U.S. Pat. Nos. 4,736,866; 5,175,383; and 5,767,337; incorporated herein by reference). In some cases, the introduced gene may be activated at a specific time in a specific tissue type during fetal development or postnatally. Expression of the transgene is monitored by analysis of phenotype or tissue-specific mRNA expression in transgenic animals before, during, and after challenge with experimental drug therapies.

Embryonic Stem Cells

Embryonic stem cells (ES) isolated from rodent embryos retain the potential to form an embryo. When ES cells are placed inside a carrier embryo, they resume normal development and contribute to all tissues of the live-born animal. ES cells are the preferred cells used in the creation of experimental knockout and knockin rodent strains. Mouse ES cells, such as the mouse 129/SvJ cell line, are derived from the early mouse embryo and are grown under culture conditions well known in the art. Vectors for knockout strains contain a disease gene candidate modified to include a marker gene which disrupts transcription and/or translation in vivo. The vector is introduced into ES cells by transformation methods such as electroporation, liposome delivery, microinjection, and the like which are well known in the art. The endogenous rodent gene is replaced by the disrupted disease gene through homologous recombination and integration during cell division. Transformed ES cells are identified, and preferably microinjected into mouse cell blastocysts such as those from the C57BL/6 mouse strain. The blastocysts are surgically transferred to pseudopregnant dams and the resulting chimeric progeny are genotyped and bred to produce heterozygous or homozygous strains.

ES cells are also used to study the differentiation of various cell types and tissues in vitro, such as neural cells, hematopoietic lineages, and cardiomyocytes (Bain et al. (1995) Dev. Biol. 168:342–357; Wiles and Keller (1991) Development 111:259–267; and Klug et al. (1996) J. Clin. Invest. 98:216–224). Recent developments demonstrate that ES cells derived from human blastocysts may also be manipulated in vitro to differentiate into eight separate cell lineages, including endoderm, mesoderm, and ectodermnal cell types (Thomson (1998) Science 282:1145–1147).

Knockout Analysis

In gene knockout analysis, a region of a human disease gene candidate is enzymatically modified to include a non-mammalian gene such as the neomycin phosphotransferase gene (neo; Capecchi (1989) Science 244:1288–1292). The inserted coding sequence disrupts transcription and translation of the targeted gene and prevents biochemical synthesis of the disease candidate protein. The modified gene is transformed into cultured embryonic stem cells (described above), the transformed cells are injected into rodent blastulae, and the blastulae are implanted into pseudopregnant dams. Transgenic progeny are crossbred to obtain homozygous inbred lines.

Knockin Analysis

Totipotent ES cells, present in the early stages of embryonic development, can be used to create knockin humanized animals (pigs) or transgenic animal models (mice or rats) of human diseases. With knockin technology, a region of a human gene is injected into animal ES cells, and the human sequence integrates into the animal cell genome by recombination. Totipotent ES cells which contain the integrated human gene are handled as described above. Inbred animals are studied and treated to obtain information on the analogous human condition. These methods have been used to model several human diseases. (See, e.g., Lee et al. (1998) Proc. Natl. Acad. Sci. 95:11371–11376; Baudoin et al. (1998) Genes Dev. 12:1202–1216; and Zhuang et al. (1998) Mol. Cell Biol. 18:3340–3349).

Non-Human Primate Model

The field of animal testing deals with data and methodology from basic sciences such as physiology, genetics, chemistry, pharmacology and statistics. These data are paramount in evaluating the effects of therapeutic agents on non-human primates as they can be related to human health. Monkeys are used as human surrogates in vaccine and drug evaluations, and their responses are relevant to human exposures under similar conditions. Cynomolgus monkeys (*Macaca fascicularis, Macaca mulata*) and common marmosets (*Callithrix jacchus*) are the most common non-human primates (NHPs) used in these investigations. Since great cost is associated with developing and maintaining a colony of NHPs, early research and toxicological studies are usually carried out in rodent models. In studies using behavioral measures such as drug addiction, NHPS are the first choice test animal. In addition, NHPS and individual humans exhibit differential sensitivities to many drugs and toxins and can be classified as "extensive metabolizers" and "poor metabolizers" of these agents.

In additional embodiments, the nucleic acid molecules which encode the mammalian protein may be used in any molecular biology techniques that have yet to be developed, provided the new techniques rely on properties of nucleic acid molecules that are currently known, including, but not limited to, such properties as the triplet genetic code and specific base pair interactions.

EXAMPLES

It is to be understood that this invention is not limited to the particular machines, materials and methods described. Although particular embodiments are described, equivalent embodiments may be used to practice the invention. The described embodiments are not intended to limit the scope of the invention which is limited only by the appended claims. The examples below are provided to illustrate the subject invention and are not included for the purpose of limiting the invention. For purposes of example, preparation of the human kidney cDNA library, KIDNNOT20, is described.

I Representative cDNA Sequence Preparation

The human kidney cDNA library KIDNNOT20 was constructed from tissue obtained from a 43-year-old Caucasian male during nephroureterectomy and unilateral left adrenalectomy. The frozen tissue was homogenized and lysed in TRIZOL reagent (1 g tissue/10 ml TRIZOL; Life Technologies), a monophasic solution of phenol and guanidine isothiocyanate, using a POLYTRON homogenizer (PT-3000; Brinkmann Instruments, Westbury N.Y.). Following homogenization, chloroform was added (1:5 v/v chloroform:homogenate), and the lysate was centrifuged. The aqueous layer was removed, and the RNA was precipitated with isopropanol. The RNA was resuspended in DEPC-treated water and digested with DNase I (Life Technologies) for 25 min at 37° C. The RNA was re-extracted with acid phenol-chloroform, pH 4.7, and precipitated using 0.3M sodium acetate and 2.5 volumes ethanol.

Messenger RNA (mRNA) was isolated using the OLI-GOTEX kit (Qiagen, Valencia Calif.) and used to construct the cDNA library. The mRNA was treated with DNaseI for 45 minutes at 25° C., precipitated using sodium acetate and ethanol, washed twice with 75% ethanol, and dissolved in DEPC-treated water. The mRNA was handled according to the recommended protocols in the SUPERSCRIPT plasmid system (Life Technologies) which contains a NotI primer-adaptor designed to prime the first strand cDNA synthesis at the poly(A) tail of mRNAs. Double stranded cDNA was blunted, ligated to EcoRI adaptors, and digested with NotI (New England Biolabs, Beverly Mass.). The cDNAs were fractionated on a SEPHAROSE CL-4B column (Amersham Pharmacia Biotech), and those cDNAs exceeding 400 bp were ligated into the NotI and EcoRI sites of the pINCY 1 plasmid (Incyte Pharmaceuticals). The plasmid was transformed into competent DH5α cells or ELECTROMAX DH10B cells (Life Technologies).

Plasmid DNA was released from the cells and purified using the REAL Prep 96 plasmid kit (Qiagen). The recommended protocol was employed except for the following changes: 1) the bacteria were cultured in 1 ml of sterile Terrific Broth (Life Technologies) with carbenicillin at 25 mg/l and glycerol at 0.4%; 2) after inoculation, the cells were cultured for 19 hours and then lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were prepared using the MICROLAB 2200 system (Hamilton, Reno Nev.) in combination with the DNA ENGINE thermal cyclers (MJ Research) and sequenced by the method of Sanger, F. and A. R. Coulson (1975; J. Mol. Biol. 94:441–448) using an ABI PRISM 377 sequencing system (PE Biosystems) or the MEGABASE 1000 DNA sequencing system (Amersham Pharmacia Biotech). Most of the isolates were sequenced according to standard ABI protocols and kits (Perkin Elmer) with solution volumes of 0.25×–1.0×concentrations. In the alternative, cDNAs were sequenced using solutions and dyes from Amersham Pharmacia Biotech.

II Identification, Assembly, and Analyses

Incyte clone 700230141H1 (SEQ ID NO:43) from ZOOSEQ database (Incyte Pharmaceuticals) of rat cDNA sequences was identified using the Library Comparisons software program (ZOOSEQ database, Incyte Pharmaceuticals). The program compares the gene expression profiles of two different cDNA libraries. The gene expression profile of the untreated rat spinal cord cDNA library RASLNOT01 library was compared with the streptozotocin-treated rat spinal cord library RASLTXT01. The gene expression profile of the RASLNOT01 library was electronically subtracted from that of the RASLTXT01 library. The nonannotated Incyte clone 700230141H1 was identified as being present only in the streptozotocin-treated tissue. Following electronic assemblage with clones derived from other rat cDNA libraries, clone 700230141H1 was used to identify human sequences in the LIFESEQ database (Incyte Pharmaceuticals) using BLAST analysis. The human sequences were annotated as imidazoline receptor subtype 1 (I-1R; W43396; SEQ ID NO:47). The first pass and extended cDNAs, SEQ ID Nos:3–29 were assembled using Phrap (P. Green). The assembled consensus, SEQ ID NO:1 was translated using MACDNASIS PRO software (Hitachi Software Engineering) to elucidate the coding region, SEQ ID NO:2. The nucleic acid and amino acid sequences were queried against databases such as the GenBank databases, SwissProt, BLOCKS, PRINTS, Prosite, and PFAM using BLAST analysis. Motifs and HMM algorithms were used to perform functional analyses, and the antigenic index (Jameson-Wolf analysis) was determined using LASERGENE software (DNASTAR). Then, the clones and assembled consensus were compared using BLAST analysis across all available mammalian libraries (ZOOSEQ database, Incyte Pharmaceuticals) to identify homologous nucleic acid molecules, SEQ ID NOs:30–46.

III Sequence Similarity

Sequence similarity was calculated as percent identity based on comparisons between at least two nucleic acid molecules or amino acid sequences using the clustal method of the LASERGENE software (DNASTAR). The clustal method uses an algorithm which groups sequences into clusters by examining the distances between all pairs. After the clusters are aligned pairwise, they are realigned in groups. Percent similarity between two sequences, sequence A and sequence B, is calculated by dividing the length of sequence A, minus the number of gap residues in sequence A, minus the number of gap residues in sequence B, into the sum of the residue matches between sequence A and sequence B, times one hundred. Gaps of very low or zero similarity between the two sequences are not included.

IV Northern Analysis

Northern analysis is a laboratory technique used to detect the presence of a transcript of a gene and involves the hybridization of a labeled probe to a membrane on which RNAs from a particular cell type or tissue have been bound.

Analogous computer techniques applying BLAST analysis were used to search for identical or related molecules in nucleotide databases such as GenBank or LIFESEQ database (Incyte Pharmaceuticals). Sequence-based analysis is much faster than membrane-based hybridization, and the sensitivity of the computer search can be modified to determine whether any particular match is categorized as exact or similar. The basis of the search is the product score which is defined as: (percent sequence identity×percent maximum BLAST score) divided by 100. The product score takes into account both the degree of similarity between two sequences and the length of the sequence match. For example, with a product score of 40, the match will be exact within a 1% to 2% error, and with a product score of at least 70, the match will be exact. Similar or related molecules are usually identified by selecting those which show product scores between 8 and 40.

The results of northern analyses are reported as a percentage distribution of libraries in which the transcript encoding the mammalian protein occurred. Analysis involved the categorization of cDNA libraries by organ/tissue and disease. The organ/tissue categories included cardiovascular, dematologic, developmental, endocrine, gastrointestinal, hematopoietic/immune, musculoskeletal, nervous, reproductive, and urologic. The disease categories included cancer, inflammation/trauma, cell proliferation, and neurological. For each category, the number of libraries expressing the sequence was counted and divided by the total number of libraries across all categories.

V Extension of Nucleic Acid Molecules

At least one of the nucleic acid molecules used to assemble SEQ ID NO:1 was produced by extension of an Incyte cDNA clone using oligonucleotide primers. One primer was synthesized to initiate 5' extension of the known fragment, and the other, to initiate 3' extension. The initial primers were designed using OLIGO 4.06 primer analysis software (National Biosciences) to be about 22 to 30 nucleotides in length, to have a GC content of about 50%, and to anneal to the target sequence at temperatures of about 55° C. to about 68° C. Any fragment which would result in hairpin structures and primer-primer dimerizations was avoided. Selected human cDNA libraries were used to extend the molecule. If more than one extension is needed, additional or nested sets of primers are designed.

High fidelity amplification was obtained by performing PCR in 96-well plates using the DNA ENGINE thermal cycler (MJ Research). The reaction mix contained DNA template, 200 nmol of each primer, reaction buffer containing $Mg^{2-}$, $(NH_4)_2SO_4$, and β-mercaptoethanol, Taq DNA polymerase (Amersham Pharmacia Biotech), ELONGASE enzyme (Life Technologies), and Pfu DNA polymerase (Stratagene), with the following parameters for primer pair selected from the plasmid: Step 1: 94° C., 3 min; Step 2: 94° C., 15 sec; Step 3: 60° C., 1 min; Step 4: 68° C., 2 min; Step 5: Steps 2, 3 and 4 repeated 20 times; Step 6: 68° C., 5 min; Step 7: storage at 4° C. In the alternative, parameters for the primer pair, T7 and SK+ (Stratagene), were as follows: Step 1: 94° C., 3 min; Step 2: 94° C., 15 sec; Step 3: 57° C., 1 min; Step 4: 68° C., 2 min; Step 5: Steps 2, 3, and 4 repeated 20 times; Step 6: 68° C., 5 min; Step 7 storage at 4° C.

The concentration of DNA in each well was determined by dispensing 100 μl PICOGREEN quantitation reagent (0.25% (v/v); Molecular Probes) dissolved in 1×TE and 0.5 μl of undiluted PCR product into each well of an opaque fluorimeter plate (Corning Costar, Acton Mass.) and allowing the DNA to bind to the reagent. The plate was scanned in a Fluoroskan II (Labsystems Oy, Helsinki, Finland) to measure the fluorescence of the sample and to quantify the concentration of DNA. A 5 μl to 10 μl aliquot of the reaction mixture was analyzed by electrophoresis on a 1% agarose mini-gel to determine which reactions were successful in producing longer sequence.

The extended sequences were desalted, concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested fragments were separated on about 0.6–0.8% agarose gels, fragments were excised as visualized under UV light, and agar removed/digested with AGARACE (Promega). Extended fragments were religated using T4 DNA ligase (New England Biolabs) into pUC 18 vector (Amersham Pharmacia Biotech), treated with Pfu DNA polymerase (Stratagene) to fill-in restriction site overhangs, and transformed into competent E. coli cells. Transformed cells were selected on antibiotic-containing media, and individual colonies were picked and cultured overnight at 37° C. in 384-well plates in LB/2×carbenicillin liquid media.

The cells were lysed, and DNA was amplified using Taq DNA polymerase (Amersham Pharmacia Biotech) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified by PICOGREEN reagent (Molecular Probes) as described above. Samples with low DNA recoveries were reamplified using the conditions described above. Samples were diluted with 20% dimethysulphoxide (1:2, v/v), and sequenced using DYENAMIC energy transfer sequencing primers and the DYENAMIC DIRECT kit (Amersham Pharmacia Biotech) or the ABI PRISM BIGDYE terminator cycle sequencing ready reaction kit (PE Biosystems).

In like manner, the nucleic acid molecule of SEQ ID NO:1 is used to obtain regulatory sequences using the procedure above, oligonucleotides designed for outward extension, and a genomic DNA library.

VI Labeling of Probes and Hybridization Analyses

Nucleic acids are isolated from a biological source and applied to a substrate for standard hybridization protocols by one of the following methods. A mixture of target nucleic acids, a restriction digest of genomic DNA, is fractionated by electrophoresis through an 0.7% agarose gel in 1×TAE [Tris-acetate-ethylenediamine tetraacetic acid (EDTA)] running buffer and transferred to a nylon membrane by capillary transfer using 20×saline sodium citrate (SSC). Alternatively, the target nucleic acids are individually ligated to a vector and inserted into bacterial host cells to form a library. Target nucleic acids are arranged on a substrate by one of the following methods. In the first method, bacterial cells containing individual clones are robotically picked and arranged on a nylon membrane. The membrane is placed on bacterial growth medium, LB agar containing carbenicillin, and incubated at 37° C. for 16 hours. Bacterial colonies are denatured, neutralized, and digested with proteinase K. Nylon membranes are exposed to UV irradiation in a STRATALINKER UV-crosslinker (Stratagene) to cross-link DNA to the membrane.

In the second method, target nucleic acids are amplified from bacterial vectors by thirty cycles of PCR using primers complementary to vector sequences flanking the insert. Amplified target nucleic acids are purified using SEPHACRYL-400 beads (Amersham Pharmacia Biotech). Purified target nucleic acids are robotically arrayed onto a glass microscope slide (Corning Science Products, Corning N.Y.). The slide is previously coated with 0.05% aminopropyl silane (Sigma-Aldrich, St. Louis Mo.) and cured at 110° C. The arrayed glass slide (microarray) is exposed to UV irradiation in a STRATALINKER UV-crosslinker (Stratagene).

cDNA probes are made from mRNA templates. Five micrograms of mRNA is mixed with 1 μg random primer (Life Technologies), incubated at 70° C. for 10 minutes, and lyophilized. The lyophilized sample is resuspended in 50 μl of 1×first strand buffer (cDNA Synthesis systems; Life Technologies) containing a dNTP mix, [α-$^{32}$P]dCTP, dithiothreitol, and MMLV reverse transcriptase (Stratagene), and incubated at 42° C. for 1–2 hours. After incubation, the probe is diluted with 42 μl dH$_2$O, heated to 95° C. for 3 minutes, and cooled on ice. mRNA in the probe is removed by alkaline degradation. The probe is neutralized, and degraded mRNA and unincorporated nucleotides are removed using a PROBEQUANT G-50 MicroColumn (Amersham Pharmacia Biotech). Probes can be labeled with fluorescent markers, Cy3-dCTP or Cy5-dCTP (Amersham Pharmacia Biotech), in place of the radionucleotide, [$^{32}$P] dCTP.

Hybridization is carried out at 65° C. in a hybridization buffer containing 0.5 M sodium phosphate (pH 7.2), 7% SDS, and 1 mM EDTA. After the substrate is incubated in hybridization buffer at 65° C. for at least 2 hours, the buffer is replaced with 10 ml of fresh buffer containing the probes. After incubation at 65° C. for 18 hours, the hybridization buffer is removed, and the substrate is washed sequentially under increasingly stringent conditions, up to 40 mM sodium phosphate, 1% SDS, 1 mM EDTA at 65° C. To detect signal produced by a radiolabeled probe hybridized on a membrane, the substrate is exposed to a PHOSPHO-RIMAGER cassette (Amersham Pharmacia Biotech), and the image is analyzed using IMAGEQUANT data analysis software (Amersham Pharmacia Biotech). To detect signals produced by a fluorescent probe hybridized on a microarray, the substrate is examined by confocal laser microscopy, and images are collected and analyzed using GEMTOOLS gene expression analysis software (Incyte Pharmaceuticals).

VII Complementary Nucleic Acid Molecules

Molecules complementary to the nucleic acid molecule, or a fragment thereof, are used to detect, decrease, or inhibit gene expression. Although use of oligonucleotides comprising from about 15 to about 30 base pairs is described, the same procedure is used with larger or smaller fragments or their derivatives (for example, PNAs). Oligonucleotides are designed using OLIGO 4.06 primer analysis software (National Biosciences) and SEQ ID NOs:1 and 3–46. To inhibit transcription by preventing promoter binding, a complementary oligonucleotide is designed to bind to the most unique 5' sequence, most preferably about 10 nucleotides before the initiation codon of the open reading frame. To inhibit translation, a complementary oligonucleotide is designed to prevent ribosomal binding to the mRNA encoding the mammalian protein.

VIII Expression of the Mammalian Protein

Expression and purification of the mammalian protein are achieved using bacterial or virus-based expression systems. For expression in bacteria, cDNA is subcloned into a vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into bacterial hosts, e.g., BL21(DE3). Antibiotic resistant bacteria express the mammalian protein upon induction with isopropyl beta-D-thiogalactopyranoside (IPTG). Expression in eukaryotic cells is achieved by infecting *Spodoptera frugiperda* (Sf9) insect cells with recombinant baculovirus, *Autographica californica* nuclear polyhedrosis virus. The polyhedrin gene of baculovirus is replaced with the mammalian cDNA by either homologous recombination or bacterial-mediated transposition involving transfer plasmid intermediates. Viral infectivity is maintained and the strong polyhedrin promoter drives high levels of cDNA transcription.

In most expression systems, the mammalian protein is synthesized as a fusion protein with, e.g., glutathione S-transferase (GST) or a peptide epitope tag, such as FLAG, permitting rapid, single-step, affinity-based purification of recombinant fusion protein from crude cell lysates. GST enables the purification of fusion proteins on immobilized glutathione under conditions that maintain protein activity and antigenicity. Following purification, the GST moiety can be proteolytically cleaved from the mammalian protein at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (Qiagen). Methods for protein expression and purification are discussed in Ausubel (supra, unit 16). Purified mammalian protein obtained by these methods can be used directly in the following activity assay.

IX Functional Assays

Protein function is assessed by expressing the sequences encoding mIR at physiologically elevated levels in mammalian cell culture. The nucleic acid molecule is subcloned into PCMV SPORT vector (Life Technologies), which contains the strong cytomegalovirus promoter, and 5–10 µg of the vector is transformed into a endothelial or hematopoietic human cell line using transformation methods well known in the art. An additional 1–2 µg of a plasmid containing sequence encoding CD64-GFP (Clontech) is co-transformed to provide a fluorescent marker to identify transformed cells using flow cytometry (FCM).

The influence of the introduced genes on expression can be assessed using purified populations of these transformed cells. Since CD64-GFP, which is expressed on the surface of transformed cells, binds to conserved regions of human immunoglobulin G (IgG), the transformed cells is separated using magnetic beads coated with either human IgG or antibody against CD64 (DYNAL, Lake Success N.Y.). mRNA is purified from the cells and analyzed by hybridization techniques.

X Production of mIR Specific Antibodies mIR is purified using polyacrylamide gel electrophoresis and used to immunize mice or rabbits. Antibodies are produced using the protocols below. Alternatively, the amino acid sequence of mIR is analyzed using LASERGENE software (DNASTAR) to determine regions of high immunogenicity. An immunogenic epitope, usually found near the C-terninus or in a hydrophilic region is selected, synthesized, and used to raise antibodies. Typically, epitopes of about 15 residues in length are produced using an ABI 431A peptide synthesizer (PE Biosystems) using Fmoc-chemistry and coupled to KLH (Sigma-Aldrich) by reaction with N-maleimidobenzoyl-N-hydroxysuccinimide ester to increase immunogenicity.

Rabbits are immunized with the epitope-KLH complex in complete Freund's adjuvant. Immunizations are repeated at intervals thereafter in incomplete Freund's adjuvant. After a minimum of seven weeks for mouse or twelve weeks for rabbit, antisera are drawn and tested for antipeptide activity. Testing involves binding the peptide to plastic, blocking with 1% bovine serum albumin, reacting with rabbit antisera, washing, and reacting with radio-iodinated goat anti-rabbit IgG. Methods well known in the art are used to determine antibody titer and the amount of complex formation.

XI Purification of Naturally Occurring Protein Using Specific Antibodies

Naturally occurring or recombinant mammalian protein is substantially purified by immunoaffinity chromatography using antibodies specific for the protein. An immunoaffinity column is constructed by covalently coupling the antibody to CNBr-activated SEPHAROSE resin (Amersham Pharmacia Biotech). Media containing the protein is passed over the immunoaffinity column, and the column is washed using high ionic strength buffers in the presence of detergent to allow preferential absorbance of the protein. After coupling, the protein is eluted from the column using a buffer of pH 2–3 or a high concentration of urea or thiocyanate ion to disrupt antibody/protein binding, and the protein is collected.

XII Screening Molecules for Specific Binding with the Nucleic Acid Molecule or Protein The nucleic acid molecule, or fragments thereof, or the protein, or portions thereof, are labeled with $^{32}$P-dCTP, Cy3-dCTP, or Cy5-dCTP (Amersham Pharmacia Biotech), or with BIODIPY or FITC (Molecular Probes, Eugene Oreg.), respectively. Libraries of candidate molecules or compounds previously arranged on a substrate are incubated in the presence of labeled nucleic acid molecule or protein. After incubation under conditions for either a nucleic acid or amino acid sequence, the substrate is washed, and any position on the substrate retaining label, which indicates specific binding or complex formation, is assayed, and the ligand is identified. Data obtained using different concentrations of the nucleic acid or protein are used to calculate affinity between the labeled nucleic acid or protein and the bound molecule.

XIII Demonstration of Protein Activity mIR, or biologically active fragments thereof, are labeled with $^{125}$I Bolton-Hunter reagent (Bolton and Hunter (1973) Biochem. J. 133:529–539). Candidate antihypertensive compounds, such as rilmenidine and agmatine, previously arrayed in the wells of a multi-well plate are incubated with the labeled mIR, washed, and any wells with labeled mIR complex are assayed. Data obtained using different concentrations of mIR are used to calculate values for the number, affinity, and association of mIR with the candidate ligand molecules.

TABLE 1

| Nucleic Acid SEQ ID NO: | Incyte Clone Number | Nucleotide Length | Source | Library Name | Overlap with SEQ ID NO:1 | Percent Identity |
|---|---|---|---|---|---|---|
| 3 | 3276916H1 | 256 | Homo sapiens | PROSBPT06 | 1–251 | |
| 4 | 2431638H1 | 208 | Homo sapiens | EOSINOT03 | 13–220 | |
| 5 | 2263366X12F1 | 493 | Homo sapiens | UTRSNOT02 | 14–504 | |
| 6 | 2526601F6 | 557 | Homo sapiens | BRAITUT21 | 23–577 | |
| 7 | 4031726H1 | 269 | Homo sapiens | BRAINOT23 | 293–561 | |
| 8 | 4014626F6 | 532 | Homo sapiens | BRAXNOT01 | 546–1078 | |
| 9 | 2263366X16F1 | 488 | Homo sapiens | UTRSN0T02 | 910–1395 | |
| 10 | 2488189F6 | 586 | Homo sapiens | LUNGN0T22 | 950–1534 | |
| 11 | 4014626T6 | 634 | Homo sapiens | BRAXNOT01 | 1082–1716 | |
| 12 | 2309651H1 | 259 | Homo sapiens | NGANNOT01 | 1281–1540 | |
| 13 | 1659790H1 | 239 | Homo sapiens | URETTUT01 | 1624–1862 | |
| 14 | 5505610H1 | 236 | Homo sapiens | BRADDIR01 | 1793–2028 | |
| 15 | 4745071H1 | 248 | Homo sapiens | BRAWNOT01 | 1972–2219 | |
| 16 | 4640790H1 | 268 | Homo sapiens | PROSTMT03 | 2058–2325 | |
| 17 | 3087155F6 | 247 | Homo sapiens | HEAONOT03 | 2076–2321 | |
| 18 | 4834547H1 | 210 | Homo sapiens | BRAWNOT01 | 2233–2442 | |
| 19 | 2482087H1 | 320 | Homo sapiens | SMCANOT01 | 2326–2645 | |
| 20 | 396596H1 | 288 | Homo sapiens | PITUNOT02 | 2510–2799 | |
| 21 | 2300531R6 | 455 | Homo sapiens | BRSTNOT05 | 2650–3103 | |
| 22 | 2858139F6 | 541 | Homo sapiens | SININOT03 | 2768–3306 | |
| 23 | 2096273R6 | 526 | Homo sapiens | BRAITUT02 | 2990–3514 | |
| 24 | 2521806H1 | 247 | Homo sapiens | BRAITUT21 | 3379–3625 | |
| 25 | 1886951F6 | 590 | Homo sapiens | BLADTUT07 | 3522–4095 | |
| 26 | 2204546H1 | 266 | Homo sapiens | SPLNFET02 | 3846–4111 | |
| 27 | 1540117R1 | 579 | Homo sapiens | SINTTUT01 | 4043–4625 | |
| 28 | 1724089F6 | 621 | Homo sapiens | PROSNOT14 | 4365–4983 | |
| 29 | 1809315F6 | 503 | Homo sapiens | PROSTUT12 | 4673–5128 | |
| 30 | 700708590H1 | 226 | Macaca fascicularis | MNBFNOT01 | 1165–1390 | 99 |
| 31 | 700720751H1 | 244 | Macaca fascicuiaris | MNBTNOT01 | 3195–3437 | 94 |
| 32 | 700705986H1 | 243 | Macaca fascicularis | MNBFNOT01 | 3361–3603 | 80 |
| 33 | 701251065H1 | 275 | Mus musculus | M0LUDIT07 | 3680–3956 | 84 |
| 34 | 701087190H1 | 249 | Mus musculus | MOLUDIT05 | 3916–4164 | 80 |
| 35 | 700329107H1 | 221 | Rattus norvegicus | RALINON04 | 601–819 | 74 |
| 36 | 700292102H1 | 309 | Rattus norvegicus | RAEPNOT01 | 1140–1452 | 75 |
| 37 | 700278887H1 | 307 | Rattus norvegicus | RATONOT02 | 2508–2816 | 83 |
| 38 | 700057363H1 | 296 | Rattus norvegicus | RASPNOT01 | 2782–3076 | 87 |
| 39 | 700810051H1 | 123 | Rattus norvegicus | RAPINOT03 | 3302–3423 | 73 |
| 40 | 700068150H1 | 283 | Rattus norvegicus | RABTNOT01 | 3423–3718 | 63 |
| 41 | 701024483H1 | 251 | Rattus norvegicus | RAFANOT02 | 3563–3813 | 82 |
| 42 | 701289331H1 | 255 | Rattus norvegicus | RABXNOT03 | 3755–4009 | 83 |
| 43 | 700230141H1 | 181 | Rattus norvegicus | RACONOT01 | 3944–4124 | 74 |
| 44 | 701273187H1 | 245 | Rattus norvegicus | RABXNOT01 | 3949–4193 | 76 |
| 45 | 700514583H1 | 343 | Rattus norvegicus | RASNNOT01 | 4092–4440 | 69 |
| 46 | 700768834H1 | 248 | Rattus norvegicus | RAHYNOT02 | 4317–4565 | 72 |

What is claimed is:

1. An isolated mammalian nucleic acid molecule encoding an amino acid sequence of SEQ ID NO:2.

2. An isolated mammalian nucleic acid molecule or the complement thereof selected from:
   a) a nucleic acid sequence of SEQ ID NO:1
   b) a nucleic acid sequence of SEQ ID NO:43.

3. The complement of the nucleic acid molecule of claim 1.

4. A probe comprising a polynucleotide of SEQ ID NO:43.

5. An expression vector comprising the nucleic acid molecule of claim 1.

6. A host cell containing the expression vector of claim 5.

7. A method for producing a protein, the method comprising the steps of:
   (a) culturing the host cell of claim 6 under conditions for the expression of the protein; and
   (b) recovering the protein from the host cell culture.

8. A method for detecting a mammalian nucleic acid molecule in a sample, the method comprising the steps of:
   (a) hybridizing the probe of claim 4 to at least one nucleic acid sequence in the sample, thereby forming a hybridization complex; and
   (b) detecting the hybridization complex, wherein the presence of the hybridization complex correlates with the presence of the mammalian nucleic acid molecule in the sample.

9. The method of claim 8 further comprising amplifying the nucleic acid molecule or a fragment thereof prior to hybridization.

10. A method of using a mammalian nucleic acid molecule or a fragment thereof to screen a library of molecules or compounds to identify at least one molecule or compound which specifically binds the nucleic acid molecule, the method comprising:
    a) combining the nucleic acid molecule of claim 1 with a library of molecules or compounds under conditions to allow specific binding; and
    b) detecting specific binding, thereby identifying a molecule or compound which specifically binds the nucleic acid molecule.

11. The method of claim 10 wherein the library is selected from DNA molecules, RNA molecules, peptide nucleic acids, artificial chromosome constructions, peptides, and proteins.

12. A method of using a mammalian nucleic acid molecule or a fragment thereof to purify a ligand which specifically binds the nucleic acid molecule from a sample, the method comprising:
    a) combining the nucleic acid molecule or a fragment thereof of claim 1 with a sample under conditions to allow specific binding;
    b) detecting specific binding between the nucleic acid molecule and a ligand;
    c) recovering the bound nucleic acid molecule; and
    d) separating the nucleic acid molecule from the ligand, thereby obtaining purified ligand.

* * * * *